US006211149B1

(12) United States Patent
Chesebro et al.

(10) Patent No.: US 6,211,149 B1
(45) Date of Patent: Apr. 3, 2001

(54) INHIBITORS OF FORMATION OF PROTEASE RESISTANT PRION PROTEIN

(75) Inventors: Bruce W. Chesebro, Corvallis; Byron W. Caughey, Hamilton, both of MT (US); Joelle Chabry, Tourrettes sur Loup (FR); Suzette Priola, Hamilton, MT (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/128,450

(22) Filed: Aug. 3, 1998

(51) Int. Cl.[7] .......................... A61K 38/00; A61K 38/43; A61K 39/00; C07K 5/00; C07K 7/00
(52) U.S. Cl. ................................ 514/12; 514/2; 530/300; 530/324; 530/350; 424/94.1; 424/185.1
(58) Field of Search ..................................... 530/324, 300, 530/350; 514/12, 2; 424/94.1, 185.1

(56) References Cited

U.S. PATENT DOCUMENTS

| 5,134,121 |   | 7/1992  | Mobley et al. .          |
|-----------|---|---------|--------------------------|
| 5,164,295 |   | 11/1992 | Kisilevsky et al. .      |
| 5,276,059 | * | 1/1994  | Caughey et al. .... 514/647 |
| 5,565,186 |   | 10/1996 | Prusiner et al. .        |
| 5,593,846 |   | 1/1997  | Schenk et al. .          |
| 5,679,530 |   | 10/1997 | Brentani et al. .        |
| 5,854,204 | * | 12/1998 | Findeis et al. .         |

FOREIGN PATENT DOCUMENTS

| 9311155    | * | 6/1993  | (WO) .............................. C07K/7/06 |
| WO 96/39834 |   | 12/1996 | (WO) . |
| WO 97/16728 |   | 5/1997  | (WO) . |

OTHER PUBLICATIONS

Bessen et al., Non–Genetic Propagation of Strain–Specific Properties of Scrapie Prion Protein, *Nature* 375:698–700 (1995).
Bossers et al., Scrapie Susceptibility–Linked Polymorphisms Modulate the In Vitro Conversion of Sheep Prion Protein to Protease–Resistant Forms, *Proc. Natl. Acad. Sci. USA* 94:4931–4936 (1997).
Caughey et al., Secondary Structure Analysis of the Scrapie–Associated Protein PrP 27–30 in Water by Infrared Spectroscopy, *Biochemistry* 30:7672–7680 (1991).
Chabry et al., Specific Inhibition of In Vitro Formation of Protease–Resistant Prion Protein by Synthetic Peptides, *Journal of Biological Chemistry* 273:13203–13207 (1998).
Come et al., A Kinetic Model for Amyloid Formation in the Prion Diseases: Importance of Seeding, *Proc. Natl. Acad. Sci. USA* 90:5959–5963 (1993).
Forloni et al., Neurotoxicity of a Prion Protein Fragment, *Nature* 362:543–546 (1993).
Gasset et al., Predicted α–helical Regions of the Prion Protein When Synthesized as Peptides Form Amyloid, *Proc. Natl. Acad. Sci. USA* 89:10940–10944 (1992).

Holscher et al., Overexpression of Nonconvertible PrP$^c$ Δ114–121 in Scrapie–Infected Mouse Neuroblastoma Cells Leads to trans–Dominant Inhibition of Wild–Type PrP$^{Sc}$ Accumulation, *Journal of Virology* 72:1153–1159 (1998).
Kaneko et al., Prion Protein (PrP) Synthetic Peptides Induce Cellular PrP to Acquire Properties of the Scrapie Isoform, *Proc. Natl. Acad. Sci. USA* 92:11160–11164 (1995).
Kaneko et al., Molecular Properties of Complexes Formed Between the Prion Protein and Synthetic Peptides, *Journal of Molecular Biology* 270:574–586 (1997).
Kocisko et al., Cell–Free Formation of Protease–Resistant Prion Protein, *Nature* 370:471–474 (1994).
Kocisko et al., Species Specificity in the Cell–Free Conversion of Prion Protein to Protease–Resistant Forms: A Model for the Scrapie Species Barrier, *Proc. Natl. Acad. Sci. USA* 92:3923–3927 (1995).
Lacorazza et al., Expression of Human β–Hexosaminidase α–Subunit Gene (the Gene Defect of Tay–Sachs Disease) in Mouse Brains Upon Engraftment of Transduced Progenitor Cells, *Nature Medicine* 2:424–429 (1996).
Pan et al., Conversion of α–Helices into β–Sheets Features in the Formation of the Scrapie Prion Proteins, *Proc. Natl. Acad. Sci. USA* 90:10962–10966 (1993).
Priola et al., Heterologous PrP Molecules Interfere with Accumulation of Protease–Resistant PrP in Scrapie–Infected Murine Neuroblastoma Cells, *Journal of Virology* 68:4873–4878 (1994).
Priola S.A. and Chesebro B., A Single Hamster PrP Amino Acid Blocks Conversion to Protease–Resistant PrP in Scrapie–Infected Mouse Neuroblastoma Cells, *Journal of Virology* 69:7754–7758 (1995).
Raymond et al., Molecular Assessment of the Potential Transmissibilities of BSE and Scrapie to Humans, *Nature* 388:285–288 (1997).
Safar et al., Conformational Transitions, Dissociation, and Unfolding of Scrapie Amyloid (Prion) Protein, *The Journal of Biological Chemistry* 268:20276–20284 (1993).
Snyder, E.Y. and Senut, M–C., The Use of Nonneuronal Cells for Gene Delivery, *Neurobiology of Disease* 4:69–102 (1997).

* cited by examiner

*Primary Examiner*—Avis M. Davenport
(74) *Attorney, Agent, or Firm*—Klarquist Sparkman Campbell & Leigh & Whinston, LLP

(57) ABSTRACT

Peptides are disclosed that inhibit the conversion of protease sensitive prion protein (PrPsen) to the protease resistant isoform (PrPres). These peptides comprise discrete fragments of prion proteins, and are shown to inhibit the in vitro conversion of PrPsen to PrPres in a cell-free system. Numerous peptides are disclosed that include at least two amino acid residues from the highly amyloidogenic region P113–120 of the PrP protein. None of these peptides conferred protease-resistance to the PrPsen molecules. The presence of residues 119 and 120 from the highly hydrophobic sequence AGAAAAGA (position 113 to 120) produced a particular inhibitory effect. The inhibition occurred with a high degree of specificity (e.g. with an IC$_{50}$ of less than about 1000 μM).

4 Claims, 7 Drawing Sheets

(3 of 7 Drawing Sheet(s) Filed in Color)

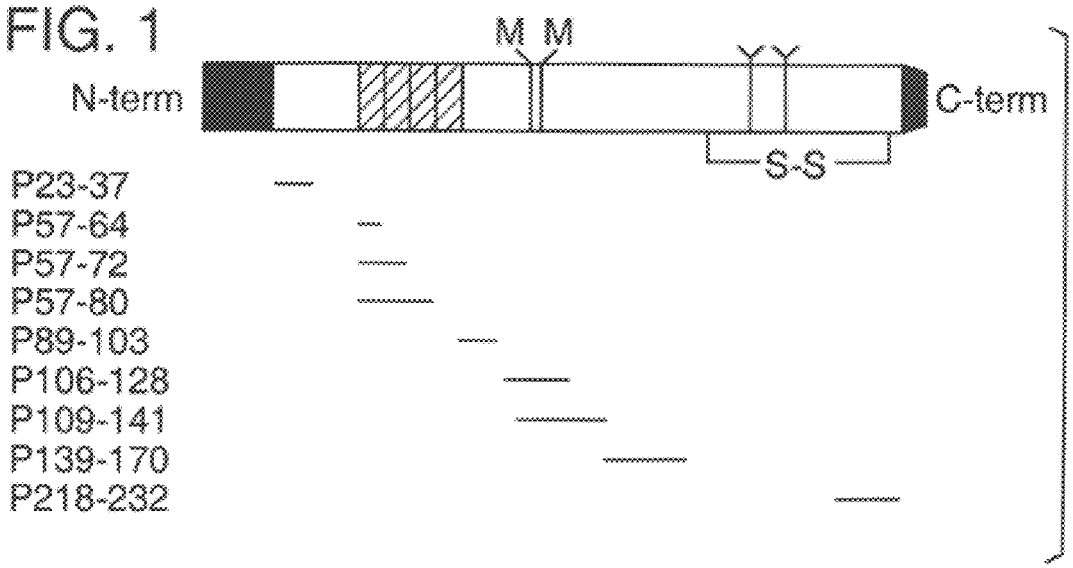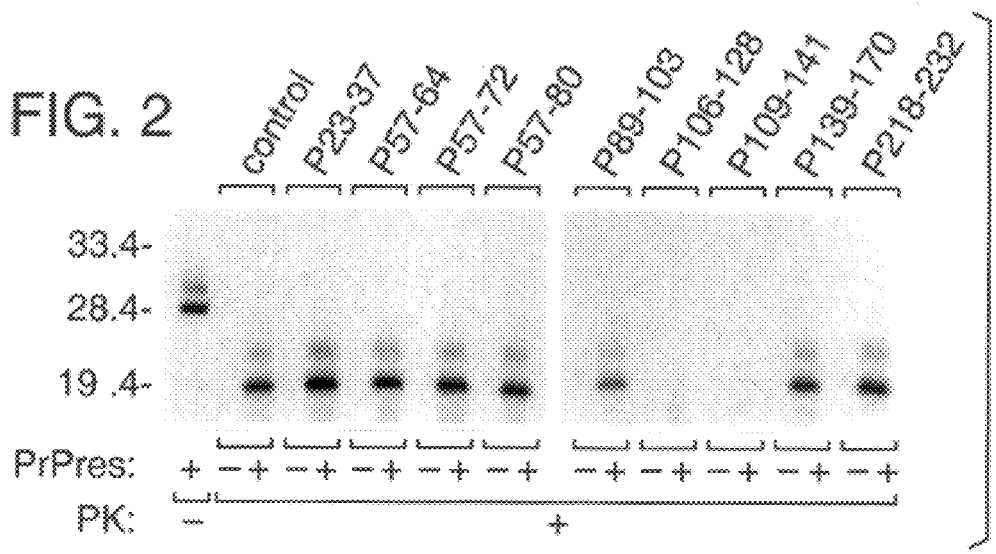

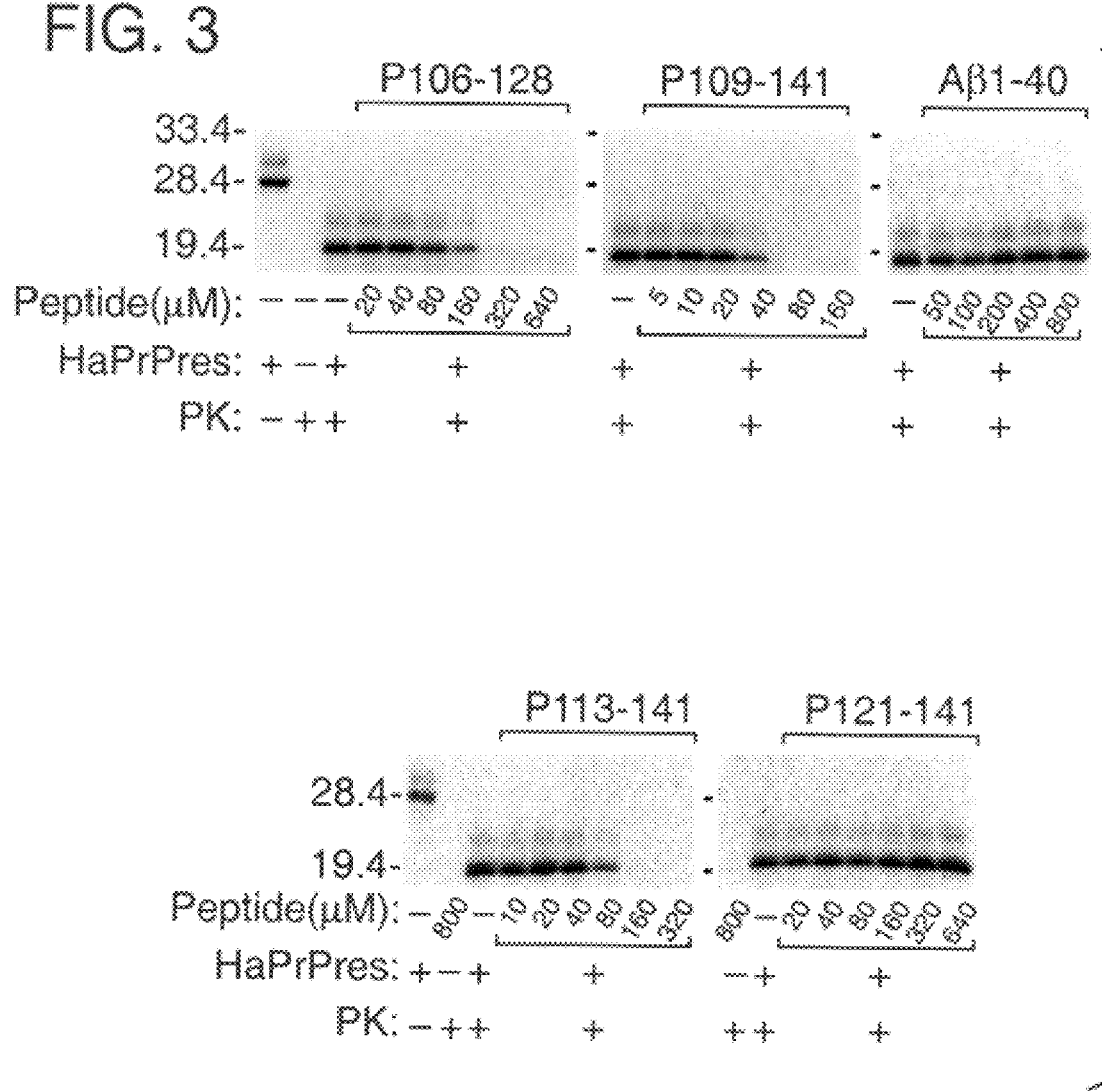

Fig. 10

```
        90        100        110        120        130        140
SHa:  G   QGGGTHNQWN KPSKPKTNMK HMAGAAAAGA VVGGLGGYML GSAMSRPMMH
Hu:   G   QGGGTHSQWN KPSKPKTNMK HMAGAAAAGA VVGGLGGYML GSAMSRPIIH 150        160        170        180        190
SHa:      FGNDWEDRYY RENMNRYPNQ VYYRPVDQYN NQNNFVHDCV NITIKQHTVT
Hu:       FGSDYEDRYY RENMHRYPNQ VYYRPMDEYS NQNNFVHDCV NITIKQHTVT 200        210        220        230       231
SHa:      TTTKGENFTE TDIKIMERVV EQMCTTQYQK ESQAYYDGRR S
Hu:       TTTKGENFTE TDVKMMERVV EQMCITQYER ESQAYYQRGS S
```

INHIBITORS OF FORMATION OF PROTEASE RESISTANT PRION PROTEIN

FIELD OF THE INVENTION

This invention concerns peptides and pharmaceutical compositions that are useful to inhibit formation of protease resistant prion proteins (PrPres), such as the protease resistant prion proteins associated with transmissible spongiform encephalopathies.

BACKGROUND OF THE INVENTION

Transmissible spongiform encephalopathies (TSE) are fatal neurodegenerative diseases that include such human disorders as sporadic and familial Creutzfeldt-Jakob disease (CJD), kuru, fatal familial insomnia, and Gerstmann-Straussler-Scheinker syndrome. Animal forms of the diseases include scrapie in sheep and bovine spongiform encephalopathy in cattle. These diseases are characterized by the formation and accumulation in the brain of an abnormal proteinase K resistant isoform (PrPres) of a normal protease-sensitive host-encoded prion protein (PrPsen). PrPres is formed from PrPsen by a post-translational process involving conformational changes that convert the PrPsen into a PrPres molecular aggregate having a higher β-sheet content. The formation of these macromolecular aggregates of PrPres is closely associated with TSE-mediated brain pathology in which amyloid deposits of PrPres are formed in the brain, which eventually becomes "spongiform" (filled with holes).

In the past, the TSE diseases were a medical curiosity because the transmissible agent was difficult to inactivate with heat, radiation or chemicals that would be expected to inactivate infectious living organisms such as bacteria and viruses. Instead, this class of diseases appeared to be transmitted by exposure to an unusual agent, for example by ritual cannibalism in the Foret people of New Guinea, or feeding of animal parts to cattle in bovine spongiform encephalopathy (BSE). Iatrogenic CJD has also been caused by administration of human growth hormone derived from cadaveric pituitaries, transplanted dura mater and corneal grafts, as well as exposure of surgeons to affected tissue during neurological procedures. The TSE diseases took on new urgency, however, when it appeared that cross-species infection of humans in Europe may have occurred, perhaps from the ingestion of beef from affected cows. That development has further stimulated an international search for a better understanding of the pathophysiological mechanism of the disease, and possible treatments.

The presence of a native prion protein (PrP) has been shown to be essential to pathogenesis of TSE. The cellular protein PrPsen is a sialoglycoprotein encoded by a gene that in humans is located on chromosome 20. The PrP gene is expressed in neural and non-neural tissues, with the highest concentration of its mRNA being in neurons. The translation product of the PrP gene consists of 253 amino acids in humans, 254 in hamsters and mice, 264 amino acids in cows, and 256 amino acids in sheep (all of these sequences are disclosed in U.S. Pat. No. 5,565,186, which describes methods of making transgenic mice that express species specific PrP. Other sequence information is included in Locht, C. et al., *Proc. Natl. Acad. Sci. USA* 83:6372–6376, 1986; Kretzschmar, H. A. et al., *DNA* 5:315–324, 1986; Yoshimoto, J. et al., *Virus Genes* 6:343–356, 1992; Goldmann, W. et al. *Proc. Natl. Acad. Sci. USA* 87:2476–2480, 1990). In prion protein related encephalopathies, the cellular PrPsen is converted into the altered PrPres that is distinguishable from PrPsen in that PrPres (1) aggregates; (2) is proteinase K resistant in that only approximately the N-terminal 67 amino acids are removed by proteinase K digestion under conditions in which PrPsen is completely degraded; and (3) has an alteration in protein conformation in which the amount of α-helical conformation for PrPsen is reduced, and the amount of β-sheet conformation for PrPres is increased.

If PrPsen is not expressed in the brain tissue of animal recipients of scrapie-infected neurografts, no pathology occurs outside the graft, demonstrating that PrPres and PrPsen are both required for the pathology (Brander et al., *Nature* 379:339–343, 1996). The long latency period between infection and the appearance of disease (months to decades depending on species) has prompted the development of a cell-free in vitro test, in which PrPres induces the conversion of PrPsen to PrPres (Kocisko et al., Nature 370:471–474, 1994). See also Prusiner et al., WO 97/16728 published May 9, 1997. The in vitro interaction between PrPres and PrPsen occurs with species and strain specificities that mimic TSE species barrier effects and strain differences in vivo (Kocisko et al., *Proc Natl Acad Sci USA* 92, 3923–3927, 1995; Bessen et al., *Nature* 375, 698–700, 1995; Bossers et al., *Proc. Natl. Acad. Sci. USA* 94, 4931–4936, 1997; Raymond et al., *Nature* 388, 285–288, 1997), hence in vitro cell free culture techniques are considered to accurately predict pathological developments in the brains of infected animals. These in vivo and in vitro observations indicate that direct interactions between PrPres and PrPsen form PrPres and promote TSE pathogenesis.

Small synthetic peptides containing certain PrP sequences have previously been shown to spontaneously aggregate to form fibrils with a high degree of β-sheet secondary structure of the type seen in the insoluble deposits in TSE afflicted brains (Gasset et al. *Proc. Natl. Acad. Sci. USA* 89, 10940–10944, 1992; Come et al., *Proc. Natl. Acad. Sci. USA* 90, 5959–5963, 1993; Forloni et al., *Nature* 362, 543–546, 1993; Hope et al., *Neurodegeneration* 5, 1–11, 1996). Moreover, other synthetic PrP peptides have been shown to interact with PrPsen molecules to form an aggregated complex with increased protease-resistance (Kaneko et al., *Proc. Natl. Acad. Sci. USA* 92, 11160–11164, 1995; Kaneko et al., *J. Mol. Biol.* 270, 574–586, 1997). The PrP derived synthetic peptide Ala Gly Ala Ala Ala Ala Gly Ala (SEQ. ID. NO. 1) from positions 113 to 120 of the PrP peptides has been described as the most highly amyloidogenic peptide in the protein (Gasset, M., et al., *Proc. Natl. Acad. Sci. USA* 89, 10940–10944, 1992), which indicates that it would be expected to promote the formation of PrPres.

Holscher et al. (J. Virol. 72: 1153–1159, 1998) recently showed that a mutant mouse PrP lacking the sequence from 114 to 121 (spanning the highly amyloidogenic region) is not converted into a proteinase K-resistant isoform after expression in scrapie-infected mouse neuroblastoma cells. This finding further supported the idea that this highly hydrophobic sequence promoted PrPres formation. U.S. Pat. No. 5,618,673 disclosed a scrapie specific palindromic oligonucleotide that hybridized to the DNA of scrapie infected tissue for use in diagnostic assays. U.S. Pat. No. 5,679,530 described a prion binding protein and peptide that were said to be useful in the non-histologic diagnosis of prion diseases.

Although these discoveries have supported the grim suggestion that certain PrP sequences can promote the formation of insoluble PrP deposits in the brain and elsewhere in the body, they have done little to provide an approach for inhibiting the formation of such deposits. However, U.S. Pat. No. 5,276,059 disclosed that mammalian diseases associated with amyloid protein formation, and the conversion of PrPsen to PrPres, could be treated by administering Congo Red dye to the mammal. U.S. Pat. No. 5,134,121 disclosed the use of a nerve growth blocking peptide to treat prion associated diseases.

Nonetheless, the need still remains for agents that will specifically inhibit the formation of PrPres, and by extension prevent or slow the deposition of amyloid deposits in the tissues of animals that have been exposed to a TSE, or are suffering from a neurodegenerative disorder having the characteristics of a spongiform encephalopathy.

SUMMARY OF THE INVENTION

The present invention takes advantage of the surprising finding that certain synthetic peptides, which incorporate the most amyloidogenic region Ala Gly Ala Ala Ala Ala Gly Ala (SEQ. ID. NO. 1) of the PrP protein, can actually inhibit the formation of PrPres under conditions where it would otherwise be formed. In one embodiment, the invention includes a purified peptide comprising or consisting essentially of XZ, where X includes at least two consecutive amino acid residues, such as the carboxy terminal residues of the dipeptide Gly Ala from SEQ. ID. NO. 1, and Z is a peptide region that, in cooperation with X, inhibits conversion of protease sensitive prion protein (PrPsen) to protease resistant prion protein (PrPres) under conditions in which PrPres would otherwise be formed. In particular embodiments, X may also be the tetrapeptide Ala Ala Gly Ala (SEQ. ID. NO. 2), the hexapeptide Ala Ala Ala Ala Gly Ala (SEQ. ID. NO. 3), or the octapeptide Ala Gly Ala Ala Ala Ala Gly Ala (SEQ. ID. NO. 1), and Z is Val Val Gly Gly Leu Gly Gly Tyr (SEQ. ID. NO. 4) or Val Val Gly Gly Leu Gly Gly Tyr Met Leu Gly Ser Ala Met Ser Arg Pro Met Met His Phe (SEQ. ID. NO. 5), Val Val Gly Gly Leu Gly Gly Tyr Met Leu Gly Ser Ala Met Ser Arg Pro Ile Ile His Phe (SEQ. ID. NO. 24) or a subsequence or variant thereof that interferes with the conversion of PrPsen to PrPres.

It has been found that even very short synthetic peptides, such as peptides consisting essentially of amino acid residues 119–128 (SEQ. ID. NO. 6), are able to inhibit the formation of PrPres. Hence the invention includes peptides XZ where X consists of at least the last two consecutive amino acids (Gly Ala) of SEQ. ID. NO. 1, and Z comprises at least the first eight amino acids of SEQ. ID. NO. 5. In more specific embodiments, X consists of at least the last four, six or eight consecutive amino acids of SEQ. ID. NO. 1, and Z consists of at least the first sixteen or even all twenty-one amino acids of SEQ. ID. NO. 5 or SEQ. ID. NO. 24. In a particularly disclosed embodiment, the purified peptide consists of SEQ. ID. NO. 8 (HaP109–141), which has an $IC_{50}$ of about 30 $\mu M$ in inhibiting the cell free conversion of PrPsen to PrPres.

In yet other embodiments, the purified peptide consists of an amino acid sequence which has an amino terminal Gly Ala motif, or a variant with conservative substitutions therein; and has a carboxyterminal motif that is homologous to at least positions 120–128 of PrP (which is conserved across all known species), such that when exposed to PrPsen in therapeutically effective amounts, the peptide specifically inhibits formation of PrPres in the presence of PrPsen, under conditions where PrPsen would otherwise be formed. The specificity of the inhibition is sufficient, in such embodiments, that the $IC_{50}$ of the inhibitory peptide is less than about 1000 $\mu M$, for example less than about 550–600 $\mu M$.

In other embodiments, the peptide comprises a subsequence of at least two amino acid residues from SEQ. ID. NO. 1, and a subsequence of SEQ. ID. NO. 13, but not a sequence of ten or more consecutive amino acid residues from positions 90–100 or 90–105 of HaPrP as shown in FIG. 10. In other embodiments, the peptide is a variant of the amino acid sequences discussed herein, but without amino acid substitutions that would be expected to change the conformation of the peptide. Substitutions that change the conformation of the synthetic peptide are avoided in these embodiments.

The invention also includes a pharmaceutical composition comprising a peptide, or a variant or mimetic thereof, and a pharmaceutically acceptable carrier or diluent. The pharmaceutical composition may be used as a diagnostic agent (for example to detect the presence of PrPres in a body fluid such as blood or cerebrospinal fluid), or may be in a unit dose form of a therapeutic agent for the treatment of spongiform encephalopathy. The invention also therefore includes a method of treating a spongiform encephalopathy, such as a TSE, by administering a therapeutically effective amount of the pharmaceutical composition to an animal that has been exposed to the transmissible agent, or which is exhibiting signs, symptoms or laboratory evidence of a TSE. If the animal is merely suspected of having been exposed to a TSE, the treatment is a prophylactic method of preventing the progression of the disease. In a situation where the animal is already believed to be exhibiting signs or symptoms of the disease, the treatment is also a method of improving the neurological or other biological condition of the animal.

The invention also includes in vitro methods for the inhibition of the conversion of PrPsen to PrPres, in which PrPsen is exposed to the inhibitory peptides in the presence of PrPres to inhibit the conversion of PrPsen to PrPres, and a method of screening for variants, analogs and mimetics of the inhibitory peptides that inhibit the conversion reaction in the assay. Also included are a specific binding agent (such as a monoclonal or polyclonal antibody) that binds an inhibitory peptide.

Also provided by the invention are nucleic acid molecules encoding the peptides disclosed herein, as well as vectors including these nucleic acid molecules.

The peptides of the present invention are particularly useful in designing analogs, derivatives or mimetics for use as a diagnostic agent or as a therapeutic inhibitor of the conversion of PrPsen to PrPres. The invention therefore also includes analogs, derivatives or mimetics of the disclosed peptides, as well as methods for screening such compounds which inhibit conversion of PrPsen to PrPres. The screening method includes contacting PrPsen with PrPres and a disclosed peptide, or peptides having one or more conservative amino acid substitutions, or analogs, derivatives or mimetics thereof, and determining whether the peptide, analog, derivative or mimetic inhibits conversion of PrPsen to PrPres.

Specific preferred embodiments of the present invention will become more evident from the following detailed description.

BRIEF DESCRIPTION OF THE DRAWINGS

FIG. 1 is a schematic representation of the hamster PrP sequence, showing localization of some of the synthetic peptides of the present invention.

FIG. 2 is an SDS-PAGE phosphor image of representative conversion reactions showing concentrations at which certain peptides inhibit conversion of PrPsen to the protease resistant form.

FIG. 3 is an SDS-PAGE phosphor image of representative conversion reactions obtained after PK digestion (PK+) in the absence (−) or presence (+) of indicated concentrations of peptides.

FIG. 10 shows the amino acid sequence of the Syrian hamster and human PrP across a comparison window at positions 90–231.

SEQUENCE LISTINGS

Figure 4:
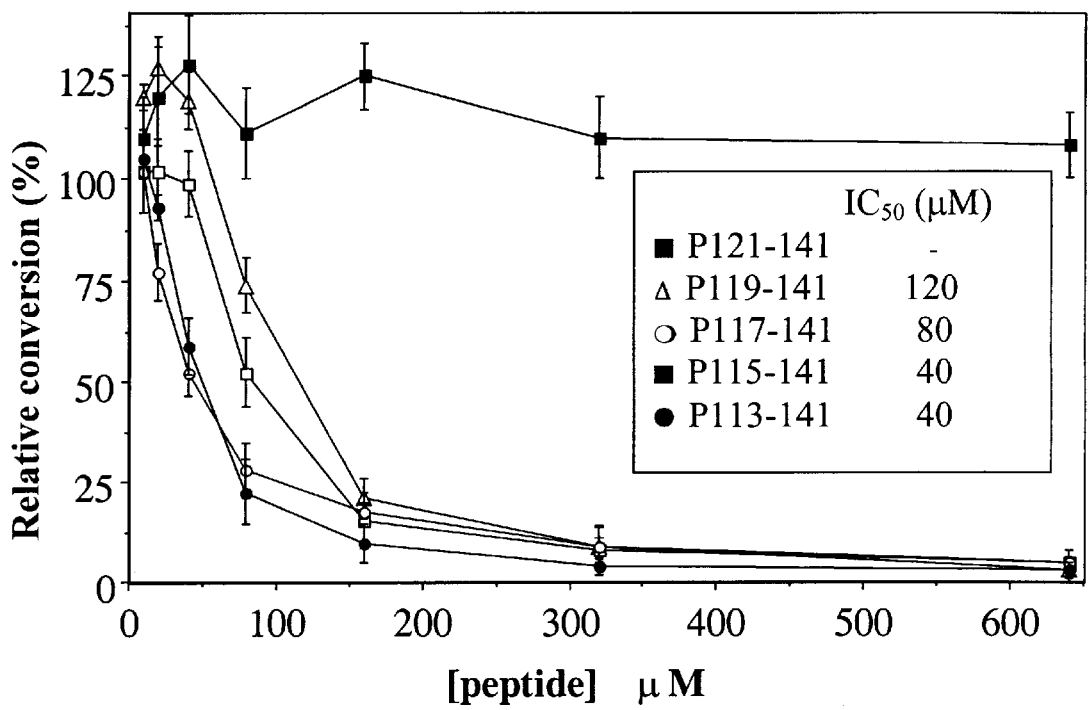
FIG. 4 is a dose response curve showing the inhibition of the conversion reaction from PrPsen to PrPres in the presence of varying concentrations of synthetic peptides: ● P113–141 (SEQ. ID. NO. 9); ○ P115–141 (SEQ. ID. NO. 10); □ P117–141 (SEQ. ID. NO. 11); Δ P119–141 (SEQ. ID. NO. 12); ■ P121–141 (SEQ. ID. NO. 13).

SEQ. ID. NO. 1 shows the amino acid sequence at positions 113–120 (P113–120) of hamster PrP (which is conserved across many mammalian species, including humans, mice, sheep and cows).

SEQ. ID. NO. 2 shows the amino acid sequence of hamster PrP at positions 117–120.

SEQ. ID. NO. 3 shows the amino acid sequence of hamster PrP at positions 115–120.

SEQ. ID. NO. 4 the amino acid sequence of hamster PrP at positions 121–128.

SEQ. ID. NO. 5 shows the amino acid sequence of hamster PrP at positions 121–141.

SEQ. ID. NO. 6 shows the amino acid sequence of hamster PrP at positions 119–128.

SEQ. ID. NO.7 shows the amino acid sequence of hamster PrP at positions 106–128.

SEQ. ID. NO. 8 shows the amino acid sequence of hamster PrP at positions 109–141.

SEQ. ID. NO.9 shows the amino acid sequence of hamster PrP at positions 113–141.

SEQ. ID. NO.10 shows the amino acid sequence of hamster PrP at positions 115–141.

SEQ. ID. NO.11 shows the amino acid sequence of hamster PrP at positions 117–141.

SEQ. ID. NO. 12 shows the amino acid sequence of hamster PrP at positions 119–141

SEQ. ID. NO.13 shows the amino acid sequence of hamster PrP at positions 121–141.

SEQ. ID. NO. 14 shows the amino acid sequence of hamster PrP at positions 119–136.

SEQ. ID. NO. 15 show the amino acid sequence of HaP109–141 (K116), SEQ. ID. NO. 16 shows the amino acid sequence of HaP109–141 (del113–116), and SEQ. ID. NO. 17 shows the amino acid sequence of MoP109–141 (which is actually Mo108–140, but has been renumbered to align with the corresponding hamster sequence), all of which are variant inhibitory peptides.

SEQ. ID. NO. 18 is HaP23–232, SEQ. ID. NO. 19 is the 254 amino acid sequence for mouse PrP, SEQ. ID. NO. 20 is the 253 amino acid sequence for human PrP, SEQ. ID. NO. 21 is the 264 amino acid sequence for bovine PrP, and SEQ. ID. NO. 22 is the 256 amino acid sequence for sheep PrP.

SEQ. ID. NO. 23 is the amino acid sequence for human PrP (HuPrP) at positions 109–141, while SEQ. ID. NO. 24 is the amino acid sequence of human PrP at positions 120–141.

SEQ. ID. NO. 25 is the DNA sequence of the open reading frame (ORF) of hamster PrP, and SEQ. ID. NO. 26 is the corresponding amino acid sequence.

SEQ. ID. NO. 27 is the DNA sequence of the ORF of mouse PrP, and SEQ. ID. NO. 28 is the corresponding amino acid sequence.

SEQ. ID. NO. 29 shows the murine amino acid sequence Mo3F4P109–141 which is a variant of MoP109–141 with Met substitutions at P109 and P112.

DETAILED DESCRIPTION OF SEVERAL EMBODIMENTS

Abbreviations and Definitions

The following abbreviations and definitions are used herein:

| | |
|---|---|
| CJD | Creutzfeldt-Jakob disease |
| Ha | Hamster |
| Hu | Human |
| Mo | Mouse |
| P | Position of an amino acid within a sequence |
| PrP | Prion protein |
| PrPsen | PrP sensitive to Proteinase K degradation |
| PrPres | PrP resistant to Proteinase K degradation |
| PK | Proteinase K |
| TSE | Transmissible spongiform encephalopathy |

Prion: An infectious agent believed to cause spongiform encephalopathies in animals (including humans). The term "prion" is a contraction of the words "protein" and "infection."

PrP protein: An animal protein that is the translation product of the PrP gene (hamster ORF shown in SEQ. ID. NO. 25 and 26 and mouse in SEQ. ID. NO. 27 and 28 as examples), wherein the protein consists of 253 amino acids in humans (SEQ. ID. NO. 20)(as disclosed in Kretzschmar et al., DNA 5:315–324, 1986; Pucket et al., Am. J. Hum. Genet. 49:320–329, 1991), 254 amino acids in hamster (as partially disclosed in SEQ. ID. NO. 18) and mice (SEQ. ID. NO. 19), 264 amino acids in cows (SEQ. ID NO. 21), and 256 amino acids in sheep (SEQ. ID. NO. 22). The amino acid sequences of all of these proteins are known, and are disclosed in U.S. Pat. No. 5,565,186, as well as in Locht, C. et al., *Proc. Natl. Acad. Sci. USA* 83:6372–6376, 1986; Kretzschmar, H. A. et al., *DNA* 5:315–324, 1986;

Yoshimoto, J. et al., *Virus Genes* 6:343–356, 1992; and Goldmann, W. et al. *Proc. Natl. Acad. Sci. USA* 87:2476–2480, 1990. The PrP protein includes a native PrPsen isoform which is degraded by proteinase K, and a pathological PrPres form which is not degraded by proteinase K, and which induces a conformational change in PrPsen to form characteristic amyloid deposits of the type seen in the spongiform encephalopathies.

The term "PrP" refers generically to peptides from animal PrP, and includes specific human, hamster, murine, sheep, bovine or avian forms of the PrP. Inhibitory PrP peptides and cDNAs are orthologs of the disclosed murine and human PrP sequences and are thus structurally related by the possession of similar amino acid and nucleic acid structures. The region from positions 119–136 of the PrP is identical in humans (P113–136), mouse (P112–119), mink, rat, sheep (P116–123), cow (P124–131), Chinese hamster and Armenian hamster. Sequences are substantially homologous across even longer regions in different species. For example mouse and human sequences are identical across a window of 113–141, except for a Ile for Met substitution at position 138 in the aligned mouse sequence. The hamster and human sequences are identical across a window of P113–141, except for a Ile for Met substitution at each of positions 138 and 139 of the human sequence. The mouse and hamster sequences are identical across a comparison window of P109–141, except for a Met to Leu substitution at each of P109 and P112, and a Met to Ile substitution in the mouse sequence.

Inhibitory PrP peptide: any peptide which, when contacted with naturally occurring or recombinant PrPsen results in the inhibition of induction of a conformational change which can be identified by the presence of enhanced β-sheet formation, increased solubility, and/or increased protease resistance relative to PrPsen. In one embodiment, the inhibitory PrP peptide is a naturally occurring, recombinant or synthetic amino acid sequence having a sequence substantially similar (e.g. 90% or greater homology, such as 95% or greater homology) to a portion of SEQ. ID. NO. 9 or 23, or a subsequence or variant thereof.

In specific embodiments, the inhibitory PrP peptide is characterized as having at least 10 contiguous amino acid residues of SEQ. ID. NO. 9 or 23, for example at least 18 contiguous amino acid residues, and in particular embodiments at least 23 contiguous amino acid residues. In particular embodiments, the contiguous amino acid residues begin at least at position 113 of the human or hamster sequence, or corresponding positions in aligned sequences of other species.

The inhibitory peptides specifically inhibit the cell free conversion of PrPsen to PrPres, in an assay of the type disclosed in Example 3, with an $IC_{50}$ of less than about 1000 $\mu$M, for example less than about 600 $\mu$M, 550 $\mu$M, 200 $\mu$M, 120 $\mu$M, or even 100 $\mu$M. Although the assay of Example 3 uses hamster PrP to determine inhibition of the conversion reaction (conversion of PrPsen to PrPres), human or other PrP may be substituted in the assay, particularly in instances where it is desired to test variants that are to be used in different species (see Example 7). For example, inhibition of the conversion reaction for human PrP may be tested by substituting human PrP for hamster PrP in the assay of Example 3.

Variant inhibitory peptides: inhibitory peptides having one or more amino acid substitutions, one or more amino acid deletions, and/or one or more amino acid insertions, so long as the peptide retains the property of inhibiting the conversion reaction. Conservative amino acid substitutions may be made in at least 1 position, for example 2, 3, 4, 5 or even 10 positions, as long as the peptide retains inhibitory activity, as readily measured by the cell free assay of inhibitory activity disclosed in the present specification. In specific embodiments, the changes, deletions, insertions, and the like, are in the sequence positions P106–118, P129–141, or P136–141, outside of the P119–128 region (SEQ. ID. NO. 10) that has been found to have highly inhibitory activity.

Conditions that would be expected to convert PrPsen to PrPres: The cell free conversion assay of Example 2, without the inhibitory peptides, in which the conversion reaction is driven by the exposure of PrPsen to PrPres (and not exposure of PrPsen to peptide fragments of PrP, as was done in Kaneko et al., *Proc. Natl. Acad. Sci. USA* 92:11160–11164, 1995). The assay of the present invention avoids conversion of PrPsen into an insoluble aggregate that is resistant to protease K, without being "specifically" resistant to protease K. The inhibition of the conversion reaction that would be expected to convert PrPsen to PrPres can be quantitated, for example by determining the percentage of the ratio between the conversion in the presence of an inhibitory peptide and the control conversion reaction in the absence of the peptide. Inhibition of "conversion" may be determined by the ratio between the PK-resistant 35S-labeled bands that are approximately 5–10 kDa lower in molecular mass than the non-digested 35S-PrPsen as quantified by phosphor autoradiographic imager analysis, as in Example 2 (with results expressed in a relative conversion percentage, as shown in FIGS. 4–7). In specific examples, the relative conversion percentage is less than 75%, 50% or particularly 25% at a peptide concentration of less than 1000 $\mu$M, for example less than 500, 250 or even 100 $\mu$M.

Sequence identity: the similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, *Methods in Molec. Biology* 24: 307–331, 1988; Higgins and Sharp, *Gene* 73:237–244, 1988; Higgins and Sharp, *CABIOS* 5:151–153, 1989; Corpet et al, *Nucleic Acids Research* 16: 10881–90, 1988; Huang et al., *Computer Applications in BioSciences* 8: 155–65,1992; and Pearson et al., *Methods in Molecular Biology* 24:307–31,1994. Altschul et al. (1994) presents a detailed consideration of sequence alignment methods and homology calculations.

The NCBI Basic Local Alignment Search Tool (BLAST) (Altschul et al., *J. Mol. Biol.* 215:403–410, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at http://www.ncbi.nlm.nih.gov/BLAST/. A description of how to determine sequence identity using this program is available at http://www.ncbi.nlm.nih.gov/BLAST/blast_help.html.

Homologs of the inhibitory PrP peptides are typically characterized by possession of at least 70% sequence identity counted over the full length alignment with the disclosed amino acid sequence of either the human, hamster, mouse, sheep, cow or other amino acid sequences using the NCBI Blast 2.0, gapped blastp set to default parameters. Such homologous peptides will more preferably possess at least 75%, more preferably at least 80% and still more preferably at least 90% or 95% sequence identity determined by this method. When less than the entire sequence is being compared for sequence identity, homologs will possess at least 75% and more preferably at least 85% and more preferably still at least 90% or 95% sequence identity over short windows of 10–20 amino acids. Methods for determining sequence identity over such short windows are described at http://www.ncbi.nlm.nih.gov/BLAST/blast_FAQs.html. One of skill in the art will appreciate that these sequence identity ranges are provided for guidance only; it is entirely possible that strongly significant homologs or other variants could be obtained that fall outside of the ranges provided.

The present invention provides not only the peptide homologs that are described above, but also nucleic acid molecules that encode such homologs.

Specific binding agent: An agent that binds substantially only to a defined target. As used herein, the term "PrP inhibitory peptide specific binding agent" includes anti-PrP inhibitory peptide antibodies and other agents that bind substantially only to the PrP inhibitory peptide. The antibodies may be monoclonal or polyclonal antibodies that are specific for the PrP inhibitory peptide, as well as immunologically effective portions ("fragments") thereof. Preferably, the antibodies used in the present invention are monoclonal antibodies (or immunologically effective portions thereof) and may also be humanized monoclonal antibodies (or immunologically effective portions thereof). Immunologically effective portions of monoclonal antibodies include Fab, Fab', F(ab')$_2$, Fabc and Fv portions (for a review, see Better and Horowitz, Methods. Enzymol. 178:476–496, 1989). Anti-inhibitory peptide antibodies may also be produced using standard procedures described in a number of texts, including "Antibodies, A Laboratory Manual" by Harlow and Lane, Cold Spring Harbor Laboratory (1988).

The determination that a particular agent binds substantially only to the inhibitory peptide may readily be made by using or adapting routine procedures. One suitable in vitro assay makes use of the Western blotting procedure (described in many standard texts, including "Antibodies, A Laboratory Manual" by Harlow and Lane). Western blotting may be used to determine that a given PrP inhibitory peptide binding agent, such as an anti-PrP inhibitory peptide monoclonal antibody, binds substantially only to the PrP inhibitory peptide.

Vector: A nucleic acid molecule as introduced into a host cell, thereby producing a transformed host cell. A vector may include nucleic acid sequences that permit it to replicate in the host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Mammal: This term includes both human and non-human mammals. Similarly, the term "subject" includes both human and veterinary subjects.

Animal: Living multicellular vertebrate organisms, a category which includes, for example, mammals and birds.

Inhibition of PrP Conversion Reaction with Inhibitory Peptides

In the present invention, novel peptides were specifically designed to interfere with conversion of PrPsen to PrPres. These peptides were obtained from a variety of subsequences of hamster PrP sequence, and were studied for their ability to inhibit the generation of PrPres under cell-free conditions. A group of peptides from the central portion of the PrP molecule having high β-sheet content displayed a strong inhibitory effect on the cell-free conversion assay. Although the disclosed assay was performed with hamster PrP, it can also be performed with hamster, mouse, sheep, bovine and human PrP. See e.g. Raymond et al., Nature 388:285–288, 1997.

EXAMPLE 1

Materials

Peptides—The following peptides were synthesized by the laboratory of molecular structure of NIH-NIAID, Rockville Md.: hamster P106–128 (SEQ. ID. NO. 7), hamster P109–141 (SEQ. ID. NO. 15), P113–141 (SEQ. ID. NO. 9) and P121–141 (SEQ. ID. NO. 13). Peptides were >95% pure and analysis by high pressure liquid chromatography revealed only a single peak. Alzheimer's disease amyloid-β-protein fragment 1–40 (Aβ 1–40) was purchased from Sigma Chemical Co. (St. Louis, Mo.). Lyophilized peptides were dissolved in deionized water at a concentration of 2 mM, distributed into 20 ml aliquots, stored at −20° C.

EXAMPLE 2

Labeling and Purification of PrPsen and PrPres

The radiolabeling and the purification of the 35S-PrPsen were performed as previously described by Raymond et al., Nature 388:285–288, 1997. Briefly, 90% confluent Syrian golden hamster brain cells were cultured for 30 min at 37° C. in 1.5 ml methionine/cysteine deficient medium followed by a 90–120 min incubation with 1.4 mCi 35S methionine/cysteine per 25 cm$^2$ flask. Then the cells were washed twice with PBS (20 mM sodium phosphate pH 7.4, 130 mM NaCl), and lysed in 1.5 ml lysis buffer containing 5 mM Tris-HCl pH 7.4, 140 mM NaCl, 5 mM EDTA, 0.5% sodium deoxycholate and 0.5% Triton. The proteins were precipitated by addition of 5 volumes of methanol, resuspended in detergent-lipid complexes, immunoprecipitated by overnight incubation at 4° C. with anti-PrP 3F4 monoclonal antibody (Kascsak et al., J. Virol. 61:3688–3693, 1987), and immune complexes were collected by binding to Protein-A sepharose beads. Radiolabeled PrPsen was eluted from sepharose beads using 0.1 M acetic acid and stored at 4° C. until use. The 35S-labeled hamster PrPsen used in this study was the glycophosphoinositol-negative form (35S-HaPrPsen) described previously (Kocisko et al., Nature 370:471–474, 1994).

PrPres was purified from brains of scrapie-infected Syrian golden hamsters by detergent lysis and differential centrifugation (Hope et al., EMBO J. 5:2591–2597, 1986). The hamsters had been infected 70 days previously with the hamster scrapie strain 263K. The yield of PrPres was determined by Western blotting using a rabbit polyclonal PrP antiserum (R27) raised against a synthetic hamster PrP peptide (residues 89 to 103) (Caughey et al., J. Virol. 65:6597–6603, 1991). The purity of the preparations was estimated at 50–60% by silver staining of SDS-PAGE gels. The hamster PrPres preparation (HaPrPres) was then diluted to 1 mg/ml in PBS containing 1% sulphobetaine 3–14 and stored at −20° C.

EXAMPLE 3

Cell-free Conversion Assay

The cell free conversion reaction was performed as previously described (Kocisko et al., Nature 370:471–474, 1994; Raymond et al., Nature 388:285–288, 1997). The purified PrPres was partially denatured with 2.5 M guanidine hydrochloride (Gdn-HCl) for 30 to 60 min at 37° C. An aliquot of 200 ng of HaPrPres, typically 8 ml, was then incubated for 40 hours at 37° C. with ~1 ng immunopurified 35S-PrPsen (12,000 cpm/reaction) in a final volume of 20 ml of conversion buffer (50 mM sodium citrate pH 6, 5 mM cetyl pyridinium chloride, 0.625% N-lauryl sarcosinate) in the presence or absence of the inhibitory peptides. At the end of the incubation time, each reaction was split 1:10, the major fraction was digested with 100 mg/ml proteinase K (PK) in Tris-saline buffer (50 mM Tris pH8, 130 mM NaCl) for 1 hour at 37° C. and the minor part (−PK) was reserved as an undigested control.

The PK reaction was stopped by the addition of 10 ml of a mixture of 4 mg/ml thyroglobulin, 20 mM pefabloc to each fraction (+ and −PK). Samples were then precipitated in 5 volumes of methanol and centrifuged for 20 min at 14,000 rpm. The pellets were resuspended in sample buffer (65 mM Tris-HCl pH6.8, 5% glycerol, 5% SDS, 4 M urea, 5% β-mercaptoethanol, 0.5% bromophenol blue), boiled 5 min and analyzed by SDS-PAGE on NOVEX pre-cast gels. The percent of the conversion was calculated by the ratio between the PK-resistant 35S-labeled bands, and the bands that are approximately 5–10 kDa lower in molecular mass than the non-digested 35S-PrPsen, as quantified by phosphor autoradiographic imager analysis. At the concentration used, none of the peptides affected the PK digestion of PrPres (data not shown).

Various PrP synthetic peptides were tested for effects on the in vitro conversion of metabolically labeled PrPsen molecules into PrPres. The localizations of some of the peptides in the primary hamster PrP sequence are shown in FIG. 1. The peptides were used in the cell-free conversion assay at a variety of concentrations, up to a final concentration of 0.8 mM. As shown in FIG. 2, the PK− (non-PK treated) 35S-HaPrPsen (in the first lane) appeared as a double band with molecular weights of 30 and 28.5 kDa, corresponding to mono and unglycosylated forms of the molecule respectively. In the absence of HaPrPres (lanes marked PrPres-) no PK-resistant bands were seen in the control experiment, indicating that none of the synthetic peptides alone were able to promote the conversion of 35S-HaPrPsen to a PK resistant form.

In the presence of 200 ng of HaPrPres (lanes marked PrPres+), but in the absence of a sufficient amount of inhibitory PrP peptide, two PK resistant 35 S-labeled bands were obtained with molecular weights of 24 and 20 kDa. FIG. 2 shows that peptides P23–37, P57–64, P57–72, P57–80, P139–170 and P218–232 failed to inhibit the conversion reaction at the concentrations tested. However, two synthetic hamster peptides, P 106–128 (SEQ. ID. NO. 7) and P 109–141 (SEQ. ID. NO. 8), were able to inhibit the formation of 35S-labeled PK-resistant PrP bands. A third peptide, P89–103, partially inhibited the conversion to PrPres.

The quantitative effect of peptide concentration on the cell-free conversion was examined further using two of the most inhibitory hamster peptides (P106–128 and P109–141), and the results are shown in FIG. 3. The peptide concentrations required to inhibit 50% of the hamster PrP conversion reaction ($IC_{50}$) were calculated to be 230 mM and 30 mM for the peptides P106–128 and P109–141 respectively (FIG. 3). In contrast, an unrelated amyloidogenic peptide, Alzheimers Aβ 1–40, was unable to inhibit the PrPsen to PrPres conversion at all concentrations tested (FIG. 3). These results clearly demonstrated that the conversion reaction was specifically inhibited, with an $IC_{50}$ of less than about 250 μM, by peptides from the central portion of PrP molecule.

EXAMPLE 4

Additional Structure Function Studies

The PrP synthetic peptide Ala Gly Ala Ala Ala Ala Gly Ala from position 113 to 120 has been described as the most highly amyloidogenic peptide in the protein (Gasset, M., et al., Proc. Natl. Acad. Sci. USA 89, 10940–10944, 1992.). To assess the influence of this sequence contained in both P106–128 and P109–141 (both of which displayed inhibitory activity), two peptides were synthesized (P113–141= SEQ. ID. NO. 9 and P121–141=SEQ. ID. NO. 13) which differed only in the hydrophobic highly amyloidogenic sequence. SEQ. ID. NO. 9 efficiently inhibited the in vitro conversion with an $IC_{50}$ value of 40 μM (FIG. 3). In contrast, P121–141 failed to inhibit the conversion at all the concentrations used (FIG. 3). When incubated with the labeled PrPsen in the absence of PrPres, none of these peptides conferred PK-resistance to PrPsen molecules (FIG. 3). Thus, the hydrophobic amyloidogenic sequence from positions 113 to 120 appeared to be active in helping provide the inhibitory effect of peptides from this region of PrP.

In order to find the minimal number of hydrophobic amino acid residues from the amyloidogenic sequence that would still provide inhibition of the conversion reaction, several partially deleted peptides were synthesized (P119–141=SEQ. ID. NO. 12, P117–141=SEQ. ID. NO. 11 and P115–141=SEQ. ID. NO. 10). The presence of two of the hydrophobic residues (Gly Ala) was sufficient to cause the inhibition of the conversion because P119–141 was nearly as inhibitory as P113–141, with an $IC_{50}$ of about 120 $\mu M$. However, the $IC_{50}$ was decreased up to three-fold as additional hydrophobic amino acid residues from the highly amyloidogenic sequence were added (FIG. 4). Whereas the $IC_{50}$ of P119–141 (positions 119–120 from the amyloidogenic sequence) was 120 $\mu M$, the $IC_{50}$ for P117–141 (positions 117–120 from the amyloidogenic sequence) was 80 $\mu M$, while the $IC_{50}$ for P115–141 (positions 115–120 from the amyloidogenic sequence) was 40 $\mu M$. Additional amino acids from the highly amyloidogenic sequence did not decrease the $IC_{50}$. For example P113–141 (with all eight amino acid residues from the highly amyloidogenic sequence) still retained an $IC_{50}$ of 40 $\mu M$, substantially the same as for P115–141 in which only six residues from the highly amyloidogenic sequence were present.

FIG. 4 is a dose response curve demonstrating the inhibition of the conversion reaction performed in the absence (0 $\mu M$) and the presence of increasing concentrations of hamster peptides (SEQ. ID. NOs. 9–13). The data in the graph represent the mean of three independent experiments and are plotted as the percentage of the ratio between the conversion in the presence of the peptide and the control conversion reaction.

EXAMPLE 5

Minimal Sequence Still Provides Inhibition

Figure 5:
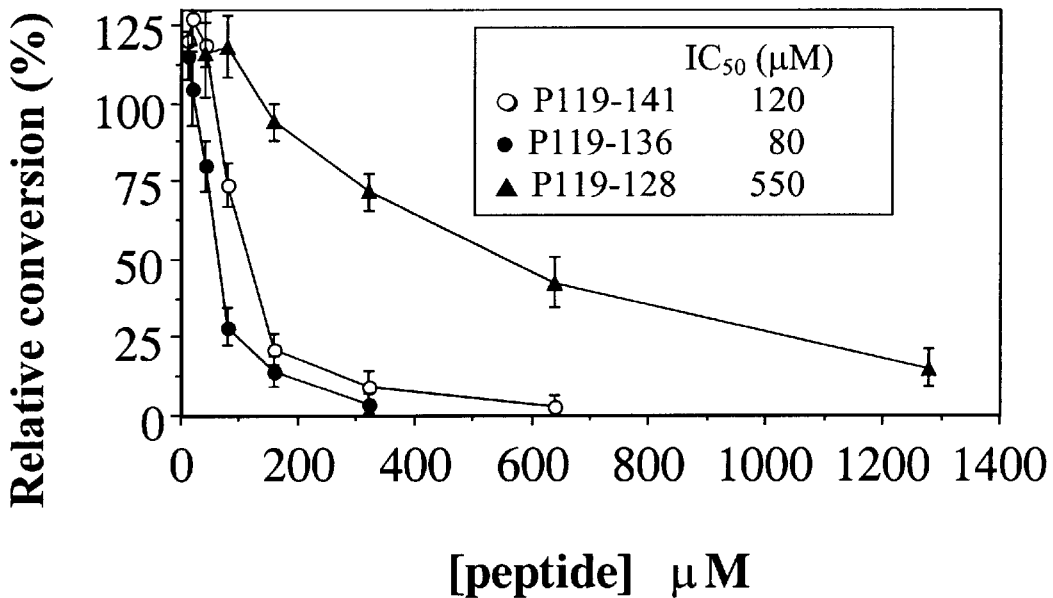
FIG. 5 is a dose response curve showing the inhibitory effect of PrP synthetic peptides ● P119–136 (SEQ. ID. NO. 14), ○ P119–141 (SEQ. ID. NO. 12) and ▲ P119–128 (SEQ. ID. NO. 6.) on the cell free conversion assay.

To further investigate minimal sequences that still provide inhibition of the conversion of PrPsen to PrPres, synthetic peptides P119–128, P119–136 and P119–141, were compared in the cell free assay, and dose response curves prepared (FIG. 5). The assays were performed as in Example 3, with 200 ng hamster 263KPrPres mixed with 12,000 cpm of immunopurified 35S-labeled hamster PrPsen in the presence of hamster peptide sequences. The data were plotted as the percentage of the ratio between the conversion in the presence of peptide and the control conversion reaction in the absence of peptide. Each point represents the mean of three independent experiments, with the standard deviation being shown as bars in FIG. 5. The $IC_{50}$ values represent the concentration of peptide capable of inhibiting 50% of the conversion reaction.

FIG. 5 demonstrates that P119–128 still retains inhibitory activity, with an $IC_{50}$ of about 550 $\mu M$. The $IC_{50}$ is reduced for the longer sequence P119–141, but is even lower for P119–130, which has the lowest $IC_{50}$ (less than 100 $\mu M$) of the three peptides.

EXAMPLE 6

Variant Peptide Inhibition Assay Studies

Additional structure function studies were performed of several more variant peptides to illustrate that the specific inhibitory activity of the peptides was retained.

Figure 6:
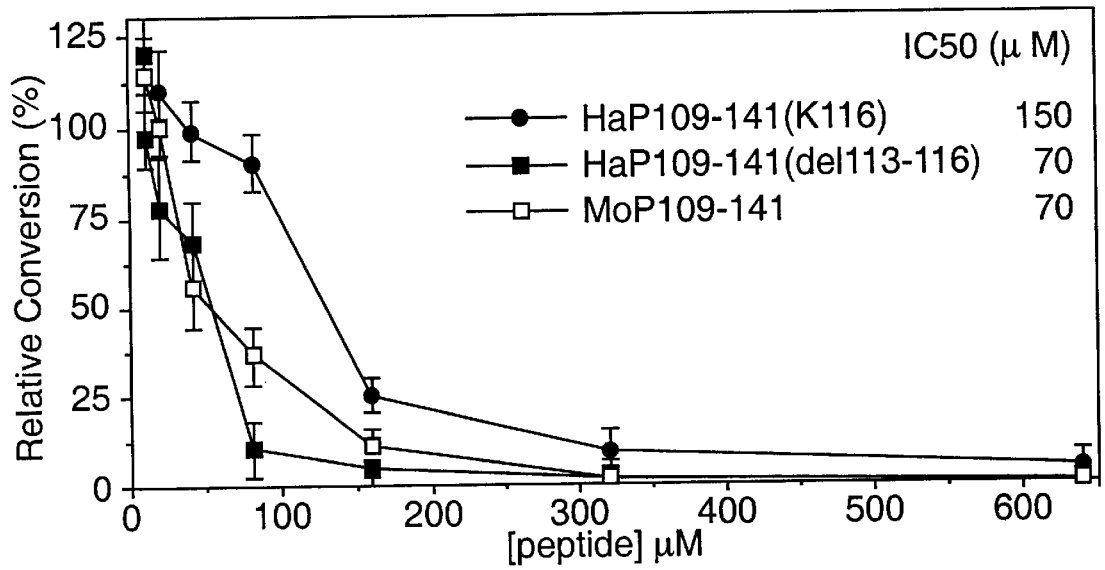
FIG. 6 is a dose response curve showing relative inhibition of the conversion reaction for several variant peptides: ● HaP109–141 (SEQ. ID. NO. 15); ■ HaP109–141 (del113–116) (SEQ. ID. NO. 16); and ○ MoP109–141 (SEQ. ID. NO. 17).

HaP109–141 (K116) (SEQ. ID. NO. 15) was synthesized using the amino acid sequence of the region 109–141 of the hamster PrP, but an Ala to Lys non-conservative substitution was made at position 116. As shown in FIG. 6, this variant still retained specific inhibitory activity, with an $IC_{50}$ of 150 $\mu M$.

HaP109–141(del113–116) (SEQ. ID. NO. 16) is a deletion variant in which positions 113–116 of the HaP109–141 sequence were deleted. FIG. 6 shows that this deletion mutant had an excellent $IC_{50}$ of 70 $\mu M$.

MoP109–141 (SEQ. ID. NO. 17) is the murine sequence instead of the hamster sequence. The murine sequence still specifically inhibited the hamster PrP conversion reaction with an excellent $IC_{50}$ of 70 $\mu M$. The hamster P113–136 sequence is conserved across both species (and indeed across multiple species such as human, mouse, hamster, cow and sheep), demonstrating that mutations outside this sequence are not deleterious to the specific inhibition reaction.

EXAMPLE 7

Murine Inhibition Assay Studies

To demonstrate that the inhibition of PrP conversion can be accomplished in other species, in addition to hamster, PrPsen and PrPres were isolated from mice (as described in Example 2) then incubated with murine synthetic peptides as described in Example 3.

MoP109–141 (SEQ. ID. NO. 17) is the amino acid sequence of the region 109–141 of the wild-type murine PrP. Mo3F4P109–141 (SEQ. ID. NO. 29) was synthesized using the amino acid sequence of the region 109–141 of the murine PrP, but non-conservative Met substitutions were made at positions 109 and 112.

Figure 7:
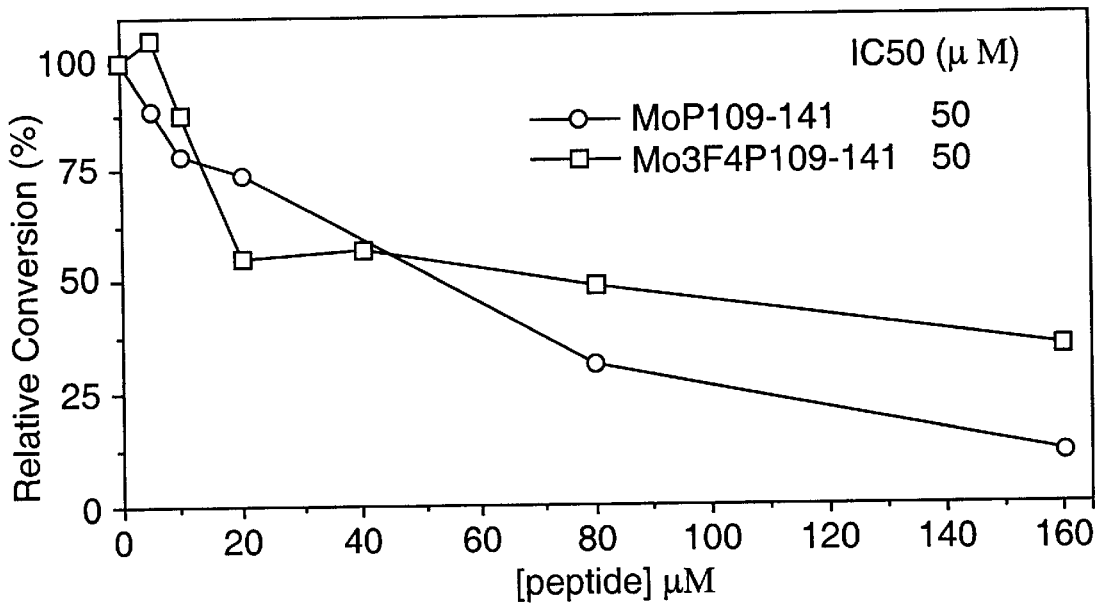
FIG. 7 is a dose response curve showing the effect of murine PrP synthetic peptides ○ MoP109–141 (SEQ. ID. NO. 17) and □ Mo3F4P109–141 (SEQ. ID. NO. 29), on murine PrP cell free conversion.

FIG. 7 demonstrates that both murine synthetic peptides inhibited murine PrP conversion with the same $IC_{50}$ of 50 $\mu M$, indicating that this method can be used to prevent PrPsen to PrPres conversion in different animal species. In addition, non-conservative substitutions at certain residues do not inhibit the conversion reaction.

EXAMPLE 8

Fourier transform infrared spectroscopy (FTIR)

Lyophilized peptides were rehydrated by mixing) with conversion buffer and incubated for 4 to 60 hours at room temperature before FTIR analysis. Samples (6 ml) were loaded into variable pathlength cells with $CaFl_2$ plates adjusted to a pathlength of 6 mm. After purging the sample chamber to reduce the water vapor contribution, spectra were collected with a Perkin-Elmer System 2000 spectrometer equipped with a MIRTGS detector. Spectral parameters were as follows: 254 scans; 4 $cm^{-1}$ resolution; 1 cm/sec OPD velocity; Kaiser-Bessel apodization. Buffer spectra were subtracted from peptide spectra to give a flat baseline in the 1800–2200 $cm^{-1}$ region. A water vapor spectrum was then subtracted to minimize the water vapor bands in the 1750–1850 $cm^{-1}$ region.

Figure 8:
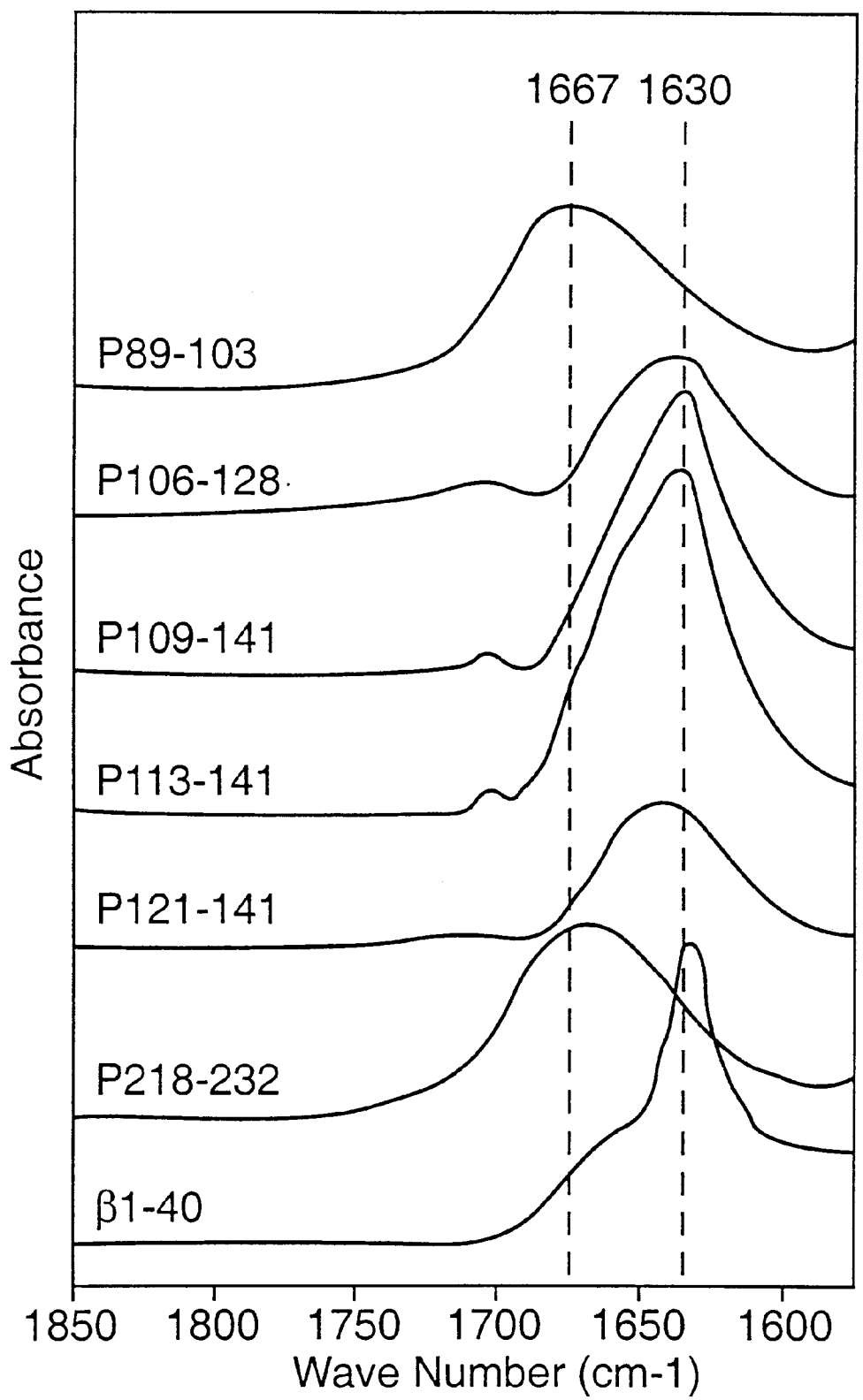
FIG. 8 shows the results of Fourier transform infrared spectroscopy for several of the peptides of the present invention, and controls, which illustrates that all the inhibitory peptides of the present invention showed evidence of high β-sheet content, as a necessary but not sufficient property for conversion inhibition.

Fourier transform infrared spectroscopy was used to compare the conformations of the PrP and Aβ 1–40 peptide to see if there was a correlation between inhibitory efficacy and conformation. The Aβ 1–40 peptide consists of P1–40 of the Alzheimer's disease amyloid P peptide, which is a β-sheet region of the much longer amyloid precursor protein. The peptides were incubated for 4–60 hours in conversion buffer without any PrPsen or PrPres. FTIR spectra of peptides incubated for 24 hours at a concentration of 2 mM are shown in FIG. 8. Five of the peptides (P106–128, P109–141, P113–141, P121–141 and Aβ 1–40) showed prominent absorbance maxima at ~1630 cm$^{-1}$ which were indicative of a high β-sheet content. For SEQ. ID. NO. 8 this predominant absorbance at 1630 cm$^{-1}$ was maintained down to concentrations of 0.2 mM. These same five peptides were at least partially insoluble as each formed a visible particulate suspension. Two other PrP peptides (P89–103 and P218–232) maintained clear solutions and had absorbance maxima near 1667 cm$^{-1}$, with no evidence of the β-sheet absorbance at ~1630 cm$^1$. Although all the inhibitory peptides showed evidence of a high β-sheet content, other peptides, such as P121–141 and Aβ 1–40, showed a similar β-sheet content but gave no inhibition of conversion. Thus, the potential to form a high amount of β-sheet structure is not sufficient for the specific inhibitory activity of any given peptide.

EXAMPLE 9

Peptide Sedimentation Studies

Considering the propensity of hydrophobic PrP peptides to aggregate in vitro, we investigated whether the inhibition of the conversion could be explained by peptide induced aggregation of 35S-HaPrPsen, which might prevent conversion of this precursor protein. For this purpose, conversion reaction mixtures were centrifuged in the presence or absence of various peptides, and pellet and supernatant fractions were analyzed for 35S-HaPrPsen.

Immunopurified 35S-HaPrPsen (12,000 cpm/reaction) was incubated for 24 hours at 37° C. with 200 ng of 2.5 M Gdn-HCl pre-treated HaPrPres in the absence or presence of indicated concentrations of peptides P109–141, P113–141, P121–141 and Aβ 1–40. At the end of the incubation time, the samples were centrifuged at room temperature for 20 min at 14,000 rpm. The supernatants and the pellets were separately collected and methanol precipitated prior to SDS-PAGE analysis and phosphor autoradiographic image quantification.

Figure 9:
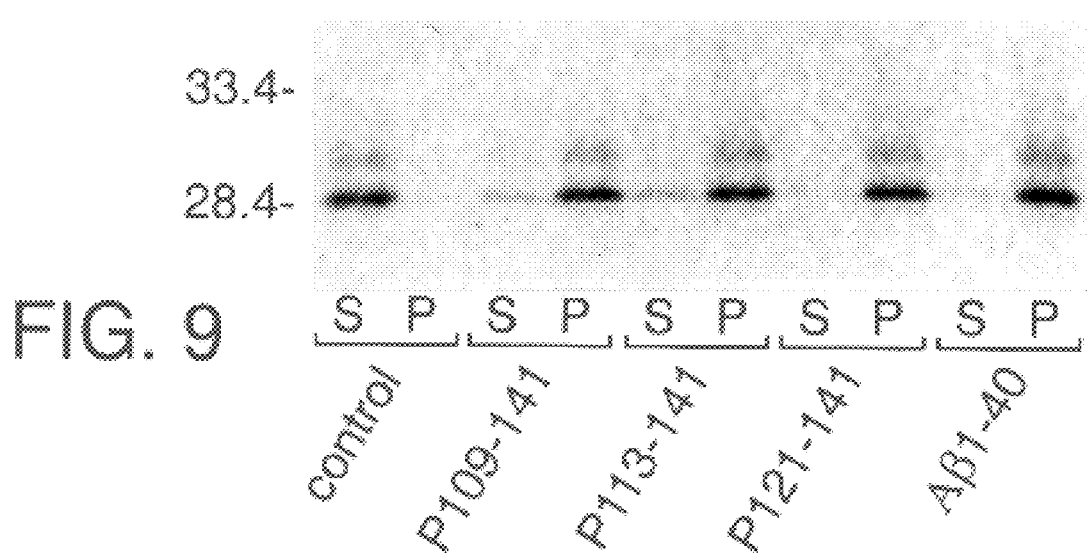
FIG. 9 is an SDS-PAGE phosphor image of supernatant (S) and pellet (P) fractions obtained by centrifugation after performing a conversion reaction by mixing S-HaPrPsen with hamster PrPres in the absence (control) or presence of certain of the peptides shown in the illustration.

Whereas 35S-HaPrPsen remained soluble in the absence of peptides, incubation with either inhibitory peptides (P 109–141 and P113–141) or non-inhibitory peptides (P121–141 and Aβ 1–40) caused aggregation and pelleting of 35S-HaPrPsen as seen in FIG. 9. Thus, although peptide induced aggregation of PrPsen occurred, this sedimentation was not sufficient for the inhibition of the conversion reaction.

EXAMPLE 10

Peptide Design

The above Examples illustrates that the PrP synthetic peptides of the present invention are involved in PrPres/PrPsen interactions, and that peptides from the central part of PrP sequence, P106–128, P109–141, or P113–141, were very efficient at inhibiting the in vitro cell-free conversion of PrPsen to PrPres (30 mM<$IC_{50}$<230 mM). The presence of the corresponding hamster sequence from 113 to 120 correlated with the inhibition of the conversion reaction. Indeed, all the peptides having this sequence such as P106–128, P109–141, or P113–141 had an inhibitory effect, whereas P121–141 did not exhibit this property. Interestingly, residues 119 and 120 appeared to be sufficient for inhibition, because P119–141 was nearly as effective as P113–141. Peptides from the amino-terminal region such as P23–37, P57–64, P57–72 and P57–80 and from the carboxy-terminal region such as P139–170 and P218–232 did not inhibit the conversion reaction. Outside of this region, only P89–103 was able to slightly decrease the conversion when incubated at the high concentration of 0.8 mM (FIG. 2). The P89–103 region is contained in the PK-resistant core of PrPres, and its location is adjacent to the most inhibitory peptide sequences. These data suggested that, unlike the central portion of PrPres, the amino and the carboxy-terminal regions of the molecule are less involved in the intermolecular interactions resulting in PrPres formation. This explanation is consistent with the fact that the carboxy and amino-terminal portions of PrPres are more sensitive to the PK digestion than the central part (Hope, J., et al., *EMBO J.* 5:2591–2597, 1986; Oesch, B., et al., *Cell* 40:735–746, 1985.).

The presence of PrP amino acid residues from 113 to 120 correlated with maximal inhibition, but other amino acid residues are involved in the specific intermolecular interaction. Positions 121–128, for example, seem to have the greatest modulating activity, but the entire modulating sequence 121–136 provides an even better $IC_{50}$ than the sequence 121–128. The adjacent sequence from 129 to 141 also appears to plays a modulatory role in the inhibition of conversion.

One skilled in the art could perform a randomized site-directed mutagenesis procedure, such as described by Huang et al., *J. Mol. Biol.* 258:688–703, 1996, or Palzkill and Botstein, *Proteins: Struct. Funct. Genet.* 14:29–44, 1992. Briefly, one or more regions of contiguous codons from either the full-length peptide, for one of the smaller synthetic peptides, is chosen for randomization. A random library is generated which contains all of the possible substitutions for the selected region. Mutated peptides are tested for their ability to prevent in vitro PrPsen to PrPres conversion as described in Example 3.

In conjunction with randomized site-directed mutagenesis, one skilled in the art could use either simple predictive algorithms (Chou and Fasman, *Biochem.* 13:222–245, 1974; Garnier et al., *J. Mol. Biol.* 120:97–120, 1978) or computer software (for example MOLSCRIPT, Kraulis, *J. Appl. Crystallog.* 24:946–950, 1991; in addition see http://hera.lmb.uni-muenchen.de/groups/gbm-pd/intsoft.html or http://www.public.iastate.edu/~pedro/research_tools.html for software and email server links) to predict the peptide secondary structure of wild-type and mutated PrP synthetic peptides. Mutated peptides that maintain the same predicted secondary structure as the wild-type peptide are tested for their ability to prevent PrPsen to PrPres conversion as described in Example 3.

The mechanism of action of the inhibitory peptides is still unclear, but the data in the above Examples indicates that the inhibitory peptides provide an effective approach to inhibiting the pathologic mechanism of conversion of PrPsen to PrPres, without themselves conferring PK resistance to 35S-PrPsen. This result is surprising in view of the reports by others that incubation of hamster PrPsen with hamster peptide P90–145 resulted in the formation of a PK-resistant, sedimentable PrPsen/peptide complex (Kaneko, K., et al., *Proc. Natl. Acad. Sci. USA* 92:11160–11164, 1995; Kaneko, K., et al., *J. Mol. Biol.* 270:574–586, 1997).

The inhibitory PrP peptides of the present invention provide new approaches for therapeutic intervention in the relentless fatal course of TSE diseases. The following examples illustrate possible peptide modifications, describe methods of therapeutic administration, and enable alternative approaches to treatment of these diseases.

EXAMPLE 11

Peptide Modifications

The present invention includes biologically active molecules that mimic the action of the inhibitory PrP peptides of the present invention, and specifically inhibit the conversion reaction from PrPsen to PrPres. The peptides of the invention include synthetic embodiments of naturally-occurring peptides described herein, as well as analogues (non-peptide organic molecules), derivatives (chemically functionalized peptide molecules obtained starting with the disclosed peptide sequences) and variants (homologs) of these peptides that specifically inhibit the conversion assay reaction. Each peptide ligand of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the peptide, whether carboxyl-terminal or side chain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide.

Hydroxyl groups of the peptide side chain may be converted to $C_1$–$C_{16}$ alkoxy or to a $C_1$–$C_{16}$ ester using well-recognized techniques. Phenyl and phenolic rings of the peptide side chain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

The activity of the peptides disclosed herein lies not in the precise amino acid sequence, but rather in the epitopes inherent in the amino acid sequences encoded by the DNA sequences. It is possible to recreate the inhibitory activity of any of these peptides by recreating the epitope, without necessarily recreating the exact amino acid sequence. This can be achieved by designing a nucleic acid sequence that encodes for the epitope, but which differs, by reason of the redundancy of the genetic code. Similarly, the DNA sequence may also be varied, while still producing a functional inhibitory peptide.

The degeneracy of the genetic code further widens the scope of the present invention as it enables major variations in the nucleotide sequence of a DNA molecule while maintaining the amino acid sequence of the encoded protein. The genetic code and variations in nucleotide codons for particular amino acids is well known. Based upon the degeneracy of the genetic code, variant DNA molecules may be derived from the DNA sequences disclosed herein using standard DNA mutagenesis techniques, or by synthesis of DNA sequences.

Additionally, standard techniques may be used to produce variant peptides which vary in amino acid sequence from the peptides encoded by the DNA molecules disclosed herein. However, such variant peptides will retain the essential characteristic of the peptides encoded by the DNA molecules disclosed herein, i.e. the ability to inhibit the conversion reaction with specificity, for example with an $IC_{50}$ of less than about 1000 $\mu$M, for example less than about 800, 550, 200, 100 or 80 $\mu$M. This inhibitory property can readily be determined by the cell free conversion reaction assay described herein. Variant peptides include those with variations in amino acid sequence, including minor deletions, additions, insertions and substitutions.

While the site for introducing an amino acid sequence variation is predetermined, the mutation per se need not be predetermined. For example, in order to optimize the performance of a mutation at a given site, random mutagenesis may be conducted at the target codon or region and the expressed peptide variants screened for the optimal combination of desired activity. Techniques for making substitution mutations at predetermined sites in DNA having a known sequence as described above are well known.

In order to maintain an optimally functional peptide, particular peptide variants will differ by only a small number of amino acids from the peptides disclosed in this specification. Such variants may have deletions (for example of 1–3 or more amino acid residues), insertions (for example of 1–3 or more residues), or substitutions that do not interfere with the desired inhibitory activity of the peptides. Substitutional variants are those in which at least one residue in the amino acid sequence has been removed and a different residue inserted in its place. In particular embodiments, such variants will have amino acid substitutions of single residues. Such substitutions generally are made in accordance with the following Table 1 when it is desired to finely modulate the characteristics of the peptide.

TABLE 1

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Greater changes in biological activity may be made by selecting substitutions that are less conservative than those in Table 1, i.e. selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Peptidomimetic and organomimetic embodiments are also within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial specific inhibitory activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", it, Klegerman & Groves, eds, 1993, *Pharmaceutical Biotechnology*, Interpharm Press: Buffalo Grove, Ill., pp. 165–174 and *Prinicples of Pharmacology* (ed. Munson, 1995), chapter 102 for a description of techniques used in CADD. Also included within the scope of the invention are mimetics prepared using such techniques that produce either peptides or conventional organic pharmaceuticals that specifically inhibit the conversion reaction as determined by the conversion assay.

EXAMPLE 12

Peptide Synthesis and Purification

The peptides provided by the present invention can be chemically synthesized by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin™ resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. (1989, *Solid Phase Peptide Synthesis*, IRL Press: Oxford).

Sasrin™ resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5–3 hours at room temperature.

Crude peptides are purified by preparative high pressure liquid chromatography (HPLC), for example using a Waters Delta-Pak C 18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

EXAMPLE 13

Recombinant Production of Peptides

Methods for the production of the inhibitory peptides of the invention from cloned genes by genetic engineering means are known in this art (even though the inhibitory peptides are not). The discussion which follows is accordingly intended as an overview of this field, and is not intended to reflect the full state of the art.

DNA encoding an inhibitory peptide may be obtained, for example, by chemical synthesis. The inhibitory peptides may be synthesized in host cells transformed with a recombinant expression construct comprising a nucleic acid encoding the inhibitory peptide cDNA. For the purposes of this invention, a recombinant expression construct is a replicable DNA construct in which a nucleic acid encoding an inhibitory peptide is operably linked to suitable control sequences capable of effecting the expression of the inhibitory peptide in a suitable host. Generally, control sequences include a transcriptional promoter, an optional operator sequence to control transcription, a sequence encoding suitable mRNA ribosomal binding sites, and sequences which control the termination of transcription and translation. See, Sambrook et al., 1990, *Molecular Cloning: A Laboratory Manual* (Cold Spring Harbor Press: New York).

Vectors useful for practicing the present invention include plasmids, viruses (including phages), retroviruses, and integratable DNA fragments (i.e., fragments integratable into the host genome by homologous recombination). Cultures of bacteria, such as *E. coli*, are an example of a possible host for recombinant inhibitory peptide synthesis. Transformed host cells are cells which have been transformed or transfected with recombinant expression constructs made using recombinant DNA techniques and comprising nucleic acid encoding an amino acid transporter protein. Transformed host cells may express the inhibitory peptides. See, Sambrook et al., ibid. In principle, any higher eukaryotic cell culture is also useful, whether from vertebrate or invertebrate culture. Propagation of such cells in cell culture has become a routine procedure. See *Tissue Culture*, Academic Press, Kruse & Patterson, editors (1973). Examples of useful host cell lines are neural progenitor cells C17-2 and C27-3, neuroblastoma cells, and other cells described in Example 15.

EXAMPLE 14

Pharmaceutical Compositions

The invention provides homogeneous compositions of the inhibitory peptides, for example a composition that is comprised of at least 90% of the peptide, variant, analog or mimetic in the composition. Such compositions are useful as diagnostic and therapeutic agents when constituted as pharmaceutical compositions with the appropriate carriers or diluents. In diagnostic embodiments, detectably-labeled peptide ligands may be used in methods for diagnosing diseases or pathological conditions by showing that the peptides are capable of inhibiting the PrPres conversion reaction that is associated with the pathogenesis of spongiform encephalopathies. Similarly, therapeutic methods of treatment are encompassed by the invention and provide using pharmaceutical compositions of such peptides administered in vivo in therapeutically-effective amounts.

Although the preferred mode of administration would be directly into the CNS where the peptides can interfere with the formation of PrPres in the brain, intravenous, intramuscular or other parenteral administration are also contemplated to interfere with PrPres formation outside the CNS. It is postulated that prion diseases have an early stage in which the infectious agent acts primarily in the lymphoreticular system (such as the spleen and lymph nodes), hence peripheral administration of the peptides could act outside the CNS to inhibit progression of the disease. Oral administration is possible, but the acidic environment of the stomach often degrades small peptides, which would complicate that mode of administration. Suppositories represent an alternative mode of administration that avoids the acidic environment of the stomach. Retrograde axoplasmic transport into the brain (from the olfactory bulb) via inhalation is also a possible mode of administration, as is ocular administration (for example in the form of eye drops, particularly if the peptide is expressed by a neurotrophic organism such as HSV).

Any of the common pharmaceutical carriers, such as sterile saline solution or sesame oil, can be used. Routes of parenteral administration include, but are not limited to, subcutaneous (sq), intracranial ventricular (icv), intrathecal (it), intravenous (iv), intramuscular (im), topical ophthalmic, subconjunctival, nasal, aural and transdermal. Peptides of the invention may be administered sq, iv or im in any conventional medium for intravenous injection, such as an aqueous saline or oil medium. The medium may also contain conventional pharmaceutical adjunct materials such as, for example, pharmaceutically acceptable salts to adjust the osmotic pressure, buffers, preservatives and the like. Among the preferred media are normal saline and sesame oil.

Embodiments of the invention comprising medicaments can be prepared with conventional pharmaceutically acceptable carriers, adjuvants and counterions as would be known to those of skill in the art. The medicaments are preferably in the form of a unit dose in solid, semi-solid and liquid dosage forms such as tablets, pills, powders, liquid solutions or suspensions, and injectable and infusible solutions, for example a unit dose vial. Effective dosage ranges included in the unit dose container can readily be determined from the effective concentrations shown in the dose response curves of FIGS. 4–7, or similar curves generated for variants, analogs, mimetics, etc.

The pharmaceutical compositions may also be administered as intranasal inhalants, for example in pharmaceutical aerosols utilizing solutions, suspensions, emulsions, powders and semisolid preparations of the type more fully described in *Remington: The Science and Practice of Pharmacy* ($19^{th}$ Edition, 1995) in chapter 95. A particular inhalant form is a metered dose inhalant containing the active ingredient, in a suspension or a dispersing agent (such as sorbitan trioleate, oleyl alcohol, oleic acid, or lecithin, and a propellant such as 12/11 or 12/114).

EXAMPLE 15

Intracerebral, Intrathecal or Intraventricular Administration

Direct intracerebral injection of the peptide is possible, or delivery can be accomplished by sustained delivery reservoirs or pumps that deliver a preselected concentration of the peptide to areas of the brain being treated. Direct CNS delivery can be directed particularly to areas of the brain that are found to be affected on an MRI scan, or delivered to areas of the brain known to be affected by the particular strain of TSE being treated.

The intrathecal injection method allows the application of small quantities of drug directly into the area surrounding the spinal cord, without surgical intervention. The peptide is then able to circulate in the cerebrospinal fluid (CSF) that is present in the subarachnoid space and in the ventricles of the brain. Intrathecal injection is achieved with disposable 30 g, ½ inch needles mated to a 10 μl luer tip syringe (Hamilton, Reno, Nev.). Drug is administered in artificial cerebrospinal fluid (CSF) and injection volumes and concentration can be determined from the dose response information given in this specification.

When the subject is a mouse, it is placed on a flat surface, with its head in a towel cupped gently with the heel of the palm, and the thumb and forefinger lightly pushing down on the iliac crests with enough force to stretch the skin across the lower back. The needle is inserted into the tissue just medial to the L5 spinous process so that it enters the groove between the spinous and transverse processes. This site maximizes vertebral accessibility and minimizes the possibility of spinal damage. The needle is then moved carefully forward to the intervertebral space as the angle of the syringe is decreased from about 30° to 15°. The tip of the needle is inserted so that approximately 0.5 cm is within the vertebral column which is reliably indicated by a flick of the mouse's tail.

In a human, conventional lumbar puncture with a spinal needle can be used to access the epidural or intrathecal space.

For icv injections, a 26 g ½ inch needle is fitted with a piece of polyethylene tubing so that 3 mm of uncovered needle enter the mouse's skull. (The sleeve ensures that the depth of the needle is appropriate for the depth of the lateral ventrical in the mouse). The needle is held at a 45° angle and inserted at Bregma, 1–2 mm lateral to midline. The needle readily punctures the skull at this suture, so no incision is required for accurate placement. The needle tip is towards the tail, and the 3 mm depth allows direct placement of the drug into a lateral ventricle. In a human, icv injections can be performed using MRI guided stereotactic procedures.

EXAMPLE 16

Administration from Producer Cell

PrP peptides delivered from producer cells can also provide inhibitory concentrations of the peptides in the brain. An example of expression of protein products by ex vivo gene transfer in neural progenitor cells is provided, for example, by an adaption of the method of Locorazza et al., *Nature Medicine* 2:424–429, 1996. Ecotropic retroviruses are produced by transfection of a GP-E86 packaging cell line with a construct containing the inhibitory peptide under transcriptional control of mouse phospho-glycerate kinase (PGK) promoter. Recipient neural progenitor cells C17-2 and C27-3 are transduced and analyzed for the presence of an unrearranged inhibitory peptide by Southern blot and polymerase chain reaction (PCR). Infected cells are then subcloned, by limiting dilution, to select those displaying the highest expression of the inhibitory peptide. The infected, peptide producing cells are transplanted into the brain of the animal to be treated, where the cells produce the inhibitory peptide to inhibit in vivo conversion of PrPsen to PrPres. The number of cells can be varied, depending on the degree to which the cells are producing the peptide, and the desired concentration of the peptide in the area of the brain being treated. Additional information about grafting neural progenitor cells into the CNS can be found in Snyder et al., *Cell* 68:33–51, 1992.

PrP variants have also been overexpressed in neuroblastoma cells, as in Holscher et al. (Holscher, C., et al., *J. Virol.* 72, 1153–1159, 1998). Neuro2a cells (purchased from the American Type Culture Collection) are maintained at 37° C. in 5% $CO_2$ in Dulbecco's modified Eagle's minimum essential medium (DMEM) supplemented with 10% heat-inactivated fetal calf serum and penicillin-streptomycin. One day before transfection, $10^6$ Neuro2a cells are plated onto 10-cm diameter dishes. Cells are transfected by the modified $CaPO_4$ precipitation protocol of Chen and Okayama, *Mol. Cell. Biol.* 7:2745–2752, 1996. The total amount of transfected DNA is adjusted (for example to 20 μg) by adding calf thymus DNA (Sigma Chemical Co.) as a carrier. After incubation for 8 to 19 hours at 35° C. and 3% $CO_2$, cells are washed with serum-free medium and then incubated with complete medium at 37° C. and 5% $CO_2$. Cells producing the PrP variant peptide can then be detected by immunoblots with specific monoclonal antibodies, or with nucleic acid probes.

Neuronal and non-neuronal cells can be grafted into the CNS for delivery of the peptide. Donor cells suitable for recombinant expression of the peptide and grafting into the CNS are discussed in Snyder et al., *Neurobiology of Disease* 4:69–102, 1997. Potential producer cells include neurons, astrocytes, oligodendrocytes, glial cells, adrenal medulla, Schwann cells, myoblasts, fibroblasts and others. Additional information about the use of producer cells and neurotrophic viral vectors (such as HSV) to deliver expression products to the CNS are given in Culver, *Gene Therapy*, 1996, chapter 5, especially pages 79–81.

MRI-guided stereotactic implantation of vector producer cells viral vectors can be accomplished as described in Culver, *Gene Therapy*, chapter 6, particularly pages 114–115.

EXAMPLE 17

DNA Vaccine

Inhibitory PrP peptides which are not themselves capable of forming PrPres could also be delivered via DNA vaccination. Examples of techniques for DNA injection for this purpose are disclosed, for example, in U.S. Pat. Nos. 5,736,524; 5,703,057; 5,721,340; 5,705,151; 5,697,901; and 5,620,896.

For example, inhibitory PrP peptide P109–141 is expressed in a recombinant DNA vector under the control of a strong promotor such as the human cytomegalovirus immediate-early promotor which has been shown to be effective in DNA vaccination studies (e.g. Foecking and Hofstetter, *Gene* 45:101–105, 1986). A concentration of 10 μg/ml of DNA in a saline solution is administered via an intravenous injection or at a peripheral site via particle bombardment (gene gun). Delivery of the DNA via intravenous injection has been show to lead to the expression of the recombinant molecule in many organs (e.g. reviewed in Hassett and Whitton *Trends in Microbiology* 4: 307–412, 1996), and both techniques have been shown to elicit protective immune responses towards infectious agents.

Another delivery method would be receptor-mediated targeting of the peptide to cells. In this instance, a protein which interacts with a cell-surface receptor is linked to the recombinant DNA and used to target the DNA to the appropriate cells for inhibition of PrPres formation (as in Wagner et al., *Proc. Natl. Acad. Sci. USA:* 89:6099–6103, 1992).

In view of the many possible embodiments to which the principles of the invention may be applied, it will recognized that the illustrated embodiment is only a preferred example of the invention, and should not be understood as a limitation on the scope of the invention. Rather, the scope of the invention is defined by the following claims. We therefore claim as our invention all that comes within the scope and spirit of these claims.

---

We claim:

1. A purified peptide consisting essentially of SEQ. ID. NO. 8, or a fragment or variant thereof, wherein the purified peptide specifically inhibits conversion of protease sensitive prion protein (PrPsen) to protease resistant prion protein (PrPres).

2. An analog, derivative or mimetic of the peptide of claim 1.

3. The purified peptide of claim 1 wherein the peptide is selected from the group consisting of SEQ. ID. NO. 9, SEQ. ID. NO. 10, SEQ. ID. NO. 11, SEQ. ID. NO. 12, SEQ. ID. NO. 14, SEQ. ID. NO. 6, or SEQ. ID. NO. 13, wherein the purified peptide specifically inhibits conversion of protease sensitive prion protein (PrPsen) to protease resistant prion protein (PrPres).

4. The purified peptide of claim 1 wherein the peptide consists of SEQ. ID. NO. 8.

* * * * *

UNITED STATES PATENT AND TRADEMARK OFFICE
CERTIFICATE OF CORRECTION

PATENT NO.    : 6,211,149 B1
DATED         : April 3, 2001
INVENTOR(S)   : Chesebro et al.

It is certified that error appears in the above-identified patent and that said Letters Patent is hereby corrected as shown below:

Title page,
After item [22], please add the following:
Item -- [60] Related U.S. Application Data
Provisional application No. 60/085,160, filed on May 12, 1998 --.

Column 1,
After the title, add: -- This application claims priority to Provisional application No. 60/085,160 filed on May 12, 1998. --

Column 5,
Line 46, "4 the" should read -- 4 shows the --.
Line 65, "141" should read -- 141. --.

Column 6,
Line 3, "show" should read -- shows --.

Column 11,
Line 54, "(12,000" should read -- (~12,000 --.

Column 12,
Line 60, "1992.)." should read -- 1992). --.

Column 14,
Line 46, "mixing) with" should read -- mixing with --.

Column 16,
Line 16, "1985.)." should read -- 1985). --.
Line 24, "plays" should read -- play --.
Line 28, "1996," should read -- 1996; --.

Column 19,
Line 20, "it, Klegerman" should read -- in Klegerman --.

UNITED STATES PATENT AND TRADEMARK OFFICE
CERTIFICATE OF CORRECTION

PATENT NO.   : 6,211,149 B1
DATED        : April 3, 2001
INVENTOR(S)  : Chesebro et al.

It is certified that error appears in the above-identified patent and that said Letters Patent is hereby corrected as shown below:

<u>Column 21,</u>
Lines 3-4, "provide using" should read -- provide useful --.

<u>Column 22,</u>
Line 40, "mouse)." should read -- mouse.) --.

<u>Column 24,</u>
Line 36, "will recognized" should read -- will be recognized --.

Signed and Sealed this

Twelfth Day of November, 2002

Attest:

JAMES E. ROGAN
*Attesting Officer*   *Director of the United States Patent and Trademark Office*

SEQUENCE LISTING

<160> NUMBER OF SEQ ID NOS: 29

<210> SEQ ID NO 1
<211> LENGTH: 8
<212> TYPE: PRT
<213> ORGANISM: Hamster sp.

<400> SEQUENCE: 1

Ala Gly Ala Ala Ala Ala Gly Ala
 1               5

<210> SEQ ID NO 2
<211> LENGTH: 4
<212> TYPE: PRT
<213> ORGANISM: Hamster sp.

<400> SEQUENCE: 2

Ala Ala Gly Ala
 1

```
<210> SEQ ID NO 3
<211> LENGTH: 6
<212> TYPE: PRT
<213> ORGANISM: Hamster sp.

<400> SEQUENCE: 3

Ala Ala Ala Ala Gly Ala
 1               5

<210> SEQ ID NO 4
<211> LENGTH: 8
<212> TYPE: PRT
<213> ORGANISM: Hamster sp.

<400> SEQUENCE: 4

Val Val Gly Gly Leu Gly Gly Tyr
 1               5

<210> SEQ ID NO 5
<211> LENGTH: 21
<212> TYPE: PRT
<213> ORGANISM: Hamster sp.

<400> SEQUENCE: 5

Val Val Gly Gly Leu Gly Gly Tyr Met Leu Gly Ser Ala Met Ser Arg
 1               5                  10                  15

Pro Met Met His Phe
            20

<210> SEQ ID NO 6
<211> LENGTH: 10
<212> TYPE: PRT
<213> ORGANISM: Hamster sp.

<400> SEQUENCE: 6

Gly Ala Val Val Gly Gly Leu Gly Gly Tyr
 1               5                  10

<210> SEQ ID NO 7
<211> LENGTH: 23
<212> TYPE: PRT
<213> ORGANISM: Hamster sp.

<400> SEQUENCE: 7

Lys Thr Asn Met Lys His Met Ala Gly Ala Ala Ala Ala Gly Ala Val
 1               5                  10                  15

Val Gly Gly Leu Gly Gly Tyr
                20

<210> SEQ ID NO 8
<211> LENGTH: 33
<212> TYPE: PRT
<213> ORGANISM: Hamster sp.

<400> SEQUENCE: 8

Met Lys His Met Ala Gly Ala Ala Ala Ala Gly Ala Val Val Gly Gly
 1               5                  10                  15

Leu Gly Gly Tyr Met Leu Gly Ser Ala Met Ser Arg Pro Met Met His
                20                  25                  30

Phe

<210> SEQ ID NO 9
```

```
<211> LENGTH: 29
<212> TYPE: PRT
<213> ORGANISM: Hamster sp.

<400> SEQUENCE: 9

Ala Gly Ala Ala Ala Ala Gly Ala Val Val Gly Gly Leu Gly Gly Tyr
 1               5                  10                  15

Met Leu Gly Ser Ala Met Ser Arg Pro Met Met His Phe
            20                  25

<210> SEQ ID NO 10
<211> LENGTH: 27
<212> TYPE: PRT
<213> ORGANISM: Hamster sp.

<400> SEQUENCE: 10

Ala Ala Ala Ala Gly Ala Val Val Gly Gly Leu Gly Gly Tyr Met Leu
 1               5                  10                  15

Gly Ser Ala Met Ser Arg Pro Met Met His Phe
            20                  25

<210> SEQ ID NO 11
<211> LENGTH: 25
<212> TYPE: PRT
<213> ORGANISM: Hamster sp.

<400> SEQUENCE: 11

Ala Ala Gly Ala Val Val Gly Gly Leu Gly Gly Tyr Met Leu Gly Ser
 1               5                  10                  15

Ala Met Ser Arg Pro Met Met His Phe
            20                  25

<210> SEQ ID NO 12
<211> LENGTH: 23
<212> TYPE: PRT
<213> ORGANISM: Hamster sp.

<400> SEQUENCE: 12

Gly Ala Val Val Gly Gly Leu Gly Gly Tyr Met Leu Gly Ser Ala Met
 1               5                  10                  15

Ser Arg Pro Met Met His Phe
            20

<210> SEQ ID NO 13
<211> LENGTH: 21
<212> TYPE: PRT
<213> ORGANISM: Hamster sp.

<400> SEQUENCE: 13

Val Val Gly Gly Leu Gly Gly Tyr Met Leu Gly Ser Ala Met Ser Arg
 1               5                  10                  15

Pro Met Met His Phe
            20

<210> SEQ ID NO 14
<211> LENGTH: 18
<212> TYPE: PRT
<213> ORGANISM: Hamster sp.

<400> SEQUENCE: 14

Gly Ala Val Val Gly Gly Leu Gly Gly Tyr Met Leu Gly Ser Ala Met
 1               5                  10                  15
```

Ser Arg

<210> SEQ ID NO 15
<211> LENGTH: 33
<212> TYPE: PRT
<213> ORGANISM: Hamster sp.

<400> SEQUENCE: 15

Met Lys His Met Ala Gly Ala Lys Ala Gly Ala Val Val Gly Gly
1               5                   10                  15

Leu Gly Gly Tyr Met Leu Gly Ser Ala Met Ser Arg Pro Met Met His
            20                  25                  30

Phe

<210> SEQ ID NO 16
<211> LENGTH: 29
<212> TYPE: PRT
<213> ORGANISM: Hamster sp.

<400> SEQUENCE: 16

Met Lys His Met Ala Ala Gly Ala Val Val Gly Gly Leu Gly Gly Tyr
1               5                   10                  15

Met Leu Gly Ser Ala Met Ser Arg Pro Met Met His Phe
            20                  25

<210> SEQ ID NO 17
<211> LENGTH: 33
<212> TYPE: PRT
<213> ORGANISM: Mus musculus

<400> SEQUENCE: 17

Leu Lys His Val Ala Gly Ala Ala Ala Gly Ala Val Val Gly Gly
1               5                   10                  15

Leu Gly Gly Tyr Met Leu Gly Ser Ala Met Ser Arg Pro Met Ile His
            20                  25                  30

Phe

<210> SEQ ID NO 18
<211> LENGTH: 208
<212> TYPE: PRT
<213> ORGANISM: Hamster sp.
<220> FEATURE:
<221> NAME/KEY: NON_TER
<222> LOCATION: (1)..(2)

<400> SEQUENCE: 18

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Gly Gly Trp Gly Gln Pro His Gly Gly Trp Gly Gln Pro His Gly
            35                  40                  45

Gly Gly Trp Gly Gln Pro His Gly Gly Trp Gly Gln Pro His Gly
        50                  55                  60

Gly Gly Trp Gly Gln Gly Gly Thr His Asn Gln Trp Asn Lys Pro
65                  70                  75                  80

Ser Lys Pro Lys Thr Asn Met Lys His Met Ala Gly Ala Ala Ala
                85                  90                  95

Gly Ala Val Val Gly Gly Leu Gly Gly Met Leu Gly Ser Ala Met Ser
                100                 105                 110

```
Arg Pro Met Met His Phe Gly Asn Asp Trp Glu Asp Arg Tyr Tyr Arg
            115                 120                 125

Glu Asn Met Asn Arg Tyr Pro Asn Gln Val Tyr Tyr Arg Pro Val Asp
        130                 135                 140

Gln Tyr Asn Asn Gln Asn Asn Phe Val His Asp Cys Val Asn Ile Thr
145                 150                 155                 160

Ile Lys Gln His Thr Val Thr Thr Thr Lys Gly Glu Asn Phe Thr
                165                 170                 175

Glu Thr Asp Ile Lys Ile Met Glu Arg Val Glu Gln Met Cys Thr
                180                 185                 190

Thr Gln Tyr Gln Lys Glu Ser Gln Ala Tyr Asp Gly Arg Arg Ser Ser
            195                 200                 205

<210> SEQ ID NO 19
<211> LENGTH: 254
<212> TYPE: PRT
<213> ORGANISM: Mus musculus

<400> SEQUENCE: 19

Met Ala Asn Leu Gly Tyr Trp Leu Leu Ala Leu Phe Val Thr Met Trp
  1               5                  10                  15

Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Thr Trp Gly Gln Pro His Gly Gly Gly Trp
     50                  55                  60

Gly Gln Pro His Gly Gly Ser Trp Gly Gln Pro His Gly Gly Ser Trp
 65                  70                  75                  80

Gly Gln Pro His Gly Gly Trp Gly Gln Gly Gly Thr His Asn
                 85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
        210                 215                 220

Tyr Asp Gly Arg Arg Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 20
<211> LENGTH: 253
<212> TYPE: PRT
```

<213> ORGANISM: Homo sapiens

<400> SEQUENCE: 20

```
Met Ala Asn Leu Gly Cys Trp Met Leu Val Leu Phe Val Ala Thr Trp
  1               5                  10                  15

Ser Asp Leu Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Gly Trp Gly Gln Pro His Gly Gly Gly
     50                  55                  60

Trp Gly Gln Pro His Gly Gly Gly Trp Gly Gln Pro His Gly Gly Gly
 65                  70                  75                  80

Trp Gly Gln Pro His Gly Gly Gly Trp Gly Gln Gly Gly Gly Thr His
                 85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

<210> SEQ ID NO 21
<211> LENGTH: 264
<212> TYPE: PRT
<213> ORGANISM: Bos taurus

<400> SEQUENCE: 21

```
Met Val Lys Ser His Ile Gly Ser Trp Ile Leu Val Leu Phe Val Ala
  1               5                  10                  15

Met Trp Ser Asp Val Gly Leu Cys Lys Lys Arg Pro Lys Pro Gly Gly
             20                  25                  30

Gly Trp Asn Thr Gly Gly Ser Arg Tyr Pro Gly Gln Gly Ser Pro Gly
         35                  40                  45

Gly Asn Arg Tyr Pro Pro Gln Gly Gly Gly Trp Gly Gln Pro His
     50                  55                  60

Gly Gly Gly Trp Gly Gln Pro His Gly Gly Trp Gly Gln Pro His
 65                  70                  75                  80

Gly Gly Gly Trp Gly Gln Pro His Gly Gly Gly Trp Gly Gln Pro His
                 85                  90                  95

Gly Gly Gly Gly Trp Gly Gln Gly Gly Thr His Gly Gln Trp Asn Lys
```

```
              100                 105                 110
Pro Ser Lys Pro Lys Thr Asn Met Lys His Val Ala Gly Ala Ala
        115                 120                 125
Ala Gly Ala Val Val Gly Leu Gly Gly Tyr Met Leu Gly Ser Ala
    130                 135                 140
Met Ser Arg Pro Leu Ile His Phe Gly Ser Asp Tyr Glu Asp Arg Tyr
145                 150                 155                 160
Tyr Arg Glu Asn Met His Arg Tyr Pro Asn Gln Val Tyr Tyr Arg Pro
                165                 170                 175
Val Asp Gln Tyr Ser Asn Gln Asn Asn Phe Val His Asp Cys Val Asn
            180                 185                 190
Ile Thr Val Lys Glu His Thr Val Thr Thr Thr Lys Gly Glu Asn
        195                 200                 205
Phe Thr Glu Thr Asp Ile Lys Met Met Glu Arg Val Val Glu Gln Met
    210                 215                 220
Cys Ile Thr Gln Tyr Gln Arg Glu Ser Gln Ala Tyr Tyr Gln Arg Gly
225                 230                 235                 240
Ala Ser Val Ile Leu Phe Ser Ser Pro Pro Val Ile Leu Leu Ile Ser
                245                 250                 255
Phe Leu Ile Phe Leu Ile Val Gly
            260

<210> SEQ ID NO 22
<211> LENGTH: 256
<212> TYPE: PRT
<213> ORGANISM: Ovis aries

<400> SEQUENCE: 22

Met Val Lys Ser His Ile Gly Ser Trp Ile Leu Val Leu Phe Val Ala
 1               5                  10                  15
Met Trp Ser Asp Val Gly Leu Cys Lys Lys Arg Pro Lys Pro Gly Gly
            20                  25                  30
Gly Trp Asn Thr Gly Gly Ser Arg Tyr Pro Gly Gln Gly Ser Pro Gly
        35                  40                  45
Gly Asn Arg Tyr Pro Pro Gln Gly Gly Gly Trp Gly Gln Pro His
    50                  55                  60
Gly Gly Gly Trp Gly Gln Pro His Gly Gly Gly Trp Gly Gln Pro His
65                  70                  75                  80
Gly Gly Gly Trp Gly Gln Pro His Gly Gly Gly Trp Gly Gln Gly
                85                  90                  95
Gly Ser His Ser Gln Trp Asn Lys Pro Ser Lys Pro Lys Thr Asn Met
            100                 105                 110
Lys His Val Ala Gly Ala Ala Ala Gly Ala Val Val Gly Gly Leu
        115                 120                 125
Gly Gly Tyr Met Leu Gly Ser Ala Met Ser Arg Pro Leu Ile His Phe
    130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Arg Tyr Ser Asn Gln Asn
                165                 170                 175
Asn Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Ile
        195                 200                 205
```

```
Met Glu Arg Val Val Glu Gln Met Cys Ile Thr Gln Tyr Gln Arg Glu
    210                 215                 220
Ser Gln Ala Tyr Tyr Gln Arg Gly Ala Ser Val Ile Leu Phe Ser Ser
225                 230                 235                 240
Pro Pro Val Ile Leu Leu Ile Ser Phe Leu Ile Phe Leu Ile Val Gly
                245                 250                 255

<210> SEQ ID NO 23
<211> LENGTH: 33
<212> TYPE: PRT
<213> ORGANISM: Homo sapiens

<400> SEQUENCE: 23

Met Lys His Met Ala Gly Ala Ala Ala Gly Ala Val Val Gly Gly
  1               5                  10                 15
Leu Gly Gly Tyr Met Leu Gly Ser Ala Met Ser Arg Pro Ile Ile His
                 20                  25                  30
Phe

<210> SEQ ID NO 24
<211> LENGTH: 21
<212> TYPE: PRT
<213> ORGANISM: Homo sapiens

<400> SEQUENCE: 24

Val Val Gly Gly Leu Gly Gly Tyr Met Leu Gly Ser Ala Met Ser Arg
  1               5                  10                  15
Pro Ile Ile His Phe
                 20

<210> SEQ ID NO 25
<211> LENGTH: 1000
<212> TYPE: DNA
<213> ORGANISM: Hamster sp.
<220> FEATURE:
<221> NAME/KEY: CDS
<222> LOCATION: (60)..(824)

<400> SEQUENCE: 25
ctcgagaatt ccgaaggcac atcgagtcca ctcgtcgcgt cggtggcaga tcagccatc      59 atg gcg aac ctt agc tac tgg ctg ctg gca ctc ttt gtg gct atg tgg     107
Met Ala Asn Leu Ser Tyr Trp Leu Leu Ala Leu Phe Val Ala Met Trp
  1               5                  10                  15 act gat gtt ggc ctc tgc aag aag cgg cca aag cct gga ggg tgg aac     155
Thr Asp Val Gly Leu Cys Lys Lys Arg Pro Lys Pro Gly Gly Trp Asn
                 20                  25                  30 act ggc gga agc cga tac cct ggg cag ggc agc cct gga ggc aac cgt     203
Thr Gly Gly Ser Arg Tyr Pro Gly Gln Gly Ser Pro Gly Gly Asn Arg
         35                  40                  45 tac cca cct cag ggt ggc ggc aca tgg ggg caa ccc cat ggt ggt ggc     251
Tyr Pro Pro Gln Gly Gly Gly Thr Trp Gly Gln Pro His Gly Gly Gly
     50                  55                  60 tgg gga cag ccc cat ggt ggt ggc tgg gga cag ccc cat ggt ggt ggc     299
Trp Gly Gln Pro His Gly Gly Gly Trp Gly Gln Pro His Gly Gly Gly
 65                  70                  75                  80 tgg ggt cag ccc cat ggt ggt ggc tgg ggt caa gga ggt ggc acc cac     347
Trp Gly Gln Pro His Gly Gly Gly Trp Gly Gln Gly Gly Gly Thr His
                 85                  90                  95 aat cag tgg aac aag ccc agt aag cca aaa acc aac atg aag cac atg     395
Asn Gln Trp Asn Lys Pro Ser Lys Pro Lys Thr Asn Met Lys His Met
                100                 105                 110
```

```
gcc ggc gct gct gcg gca ggg gcc gtg gtg ggg ggc ctt ggt ggc tac    443
Ala Gly Ala Ala Ala Gly Ala Val Val Gly Gly Leu Gly Gly Tyr
        115                 120                 125 atg ctg ggg agt gcc atg agc agg ccc atg atg cat ttt ggc aat gac    491
Met Leu Gly Ser Ala Met Ser Arg Pro Met Met His Phe Gly Asn Asp
130                 135                 140 tgg gag gac cgc tac tac cgt gaa aac atg aac cgc tac cct aac caa    539
Trp Glu Asp Arg Tyr Tyr Arg Glu Asn Met Asn Arg Tyr Pro Asn Gln
145                 150                 155                 160 gtg tat tac cgg cca gtg gac cag tac aac aac cag aac aac ttt gtg    587
Val Tyr Tyr Arg Pro Val Asp Gln Tyr Asn Asn Gln Asn Asn Phe Val
                165                 170                 175 cac gat tgt gtc aac atc acc atc aag cag cac aca gtc acc acc acc    635
His Asp Cys Val Asn Ile Thr Ile Lys Gln His Thr Val Thr Thr Thr
            180                 185                 190 acc aag ggg gag aac ttc acg gag acc gac atc aag ata atg gag cgc    683
Thr Lys Gly Glu Asn Phe Thr Glu Thr Asp Ile Lys Ile Met Glu Arg
        195                 200                 205 gtg gtg gag cag atg tgt acc acc cag tat cag aag gag tcc cag gcc    731
Val Val Glu Gln Met Cys Thr Thr Gln Tyr Gln Lys Glu Ser Gln Ala
    210                 215                 220 tac tac gat gga aga agg tcc agc gcg gtg ctg ttc tcc tcc cct cct    779
Tyr Tyr Asp Gly Arg Arg Ser Ser Ala Val Leu Phe Ser Ser Pro Pro
225                 230                 235                 240 gtg atc ctc ctc att tcc ttt ctc atc ttc ctg atg gtg gga tga        824
Val Ile Leu Leu Ile Ser Phe Leu Ile Phe Leu Met Val Gly
                245                 250 aggaagcctc cctgcttgta cttcctcgtt cttgtggtct aggctggggg aggggttatc    884
caccgtagct cttttaattg aggtggtgtc tcattcctgc ttctctttgt cccccatagg    944
ctaatgccct tggcactagt gggccctggg aatgtacagt cgataagctc ctcgag       1000

<210> SEQ ID NO 26
<211> LENGTH: 254
<212> TYPE: PRT
<213> ORGANISM: Hamster sp.

<400> SEQUENCE: 26

Met Ala Asn Leu Ser Tyr Trp Leu Leu Ala Leu Phe Val Ala Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly
    50                  55                  60

Trp Gly Gln Pro His Gly Gly Trp Gly Gln Pro His Gly Gly Gly
 65                  70                  75                  80

Trp Gly Gln Pro His Gly Gly Gly Trp Gly Gln Gly Gly Thr His
                 85                  90                  95

Asn Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
    130                 135                 140

Trp Glu Asp Arg Tyr Tyr Arg Glu Asn Met Asn Arg Tyr Pro Asn Gln
```

```
                145                 150                 155                 160
Val Tyr Tyr Arg Pro Val Asp Gln Tyr Asn Gln Asn Asn Phe Val
                    165                 170                 175

His Asp Cys Val Asn Ile Thr Ile Lys Gln His Thr Val Thr Thr Thr
                180                 185                 190

Thr Lys Gly Glu Asn Phe Thr Glu Thr Asp Ile Lys Ile Met Glu Arg
            195                 200                 205

Val Val Glu Gln Met Cys Thr Thr Gln Tyr Gln Lys Glu Ser Gln Ala
        210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Met Val Gly
                245                 250

<210> SEQ ID NO 27
<211> LENGTH: 1322
<212> TYPE: DNA
<213> ORGANISM: Mus musculus
<220> FEATURE:
<221> NAME/KEY: CDS
<222> LOCATION: (101)..(865)

<400> SEQUENCE: 27
gaattccttc agaactgaac catttcaacc gagctgaagc attctgcctt cctagtggta      60
ccagtccaat ttaggagagc caagcagact atcagtcatc atg gcg aac ctt ggc      115
                                             Met Ala Asn Leu Gly
                                               1               5 tac tgg ctg ctg gcc ctc ttt gtg act atg tgg act gat gtc ggc ctc      163
Tyr Trp Leu Leu Ala Leu Phe Val Thr Met Trp Thr Asp Val Gly Leu
             10                  15                  20 tgc aaa aag cgg cca aag cct gga ggg tgg aac acc ggt gga agc cgg      211
Cys Lys Lys Arg Pro Lys Pro Gly Gly Trp Asn Thr Gly Gly Ser Arg
         25                  30                  35 tat ccc ggg cag gga agc cct gga ggc aac cgt tac cca cct cag ggt      259
Tyr Pro Gly Gln Gly Ser Pro Gly Gly Asn Arg Tyr Pro Pro Gln Gly
     40                  45                  50 ggc acc tgg ggg cag ccc cac ggt ggt ggc tgg gga caa ccc cat ggg      307
Gly Thr Trp Gly Gln Pro His Gly Gly Gly Trp Gly Gln Pro His Gly
 55                  60                  65 ggc agc tgg gga caa cct cat ggt ggt agt tgg ggt cag ccc cat ggc      355
Gly Ser Trp Gly Gln Pro His Gly Gly Ser Trp Gly Gln Pro His Gly
 70                  75                  80                  85 ggt gga tgg ggc caa gga ggg ggt acc cat aat cag tgg aac aag ccc      403
Gly Gly Trp Gly Gln Gly Gly Gly Thr His Asn Gln Trp Asn Lys Pro
                 90                  95                 100 agc aaa cca aaa acc aac ctc aag cat gtg gca ggg gct gcg gca gct      451
Ser Lys Pro Lys Thr Asn Leu Lys His Val Ala Gly Ala Ala Ala Ala
            105                 110                 115 ggg gca gta gtg ggg ggc ctt ggt ggc tac atg ctg ggg agc gcc gtg      499
Gly Ala Val Val Gly Gly Leu Gly Gly Tyr Met Leu Gly Ser Ala Val
        120                 125                 130 agc agg ccc atg atc cat ttt ggc aac gac tgg gag gac cgc tac tac      547
Ser Arg Pro Met Ile His Phe Gly Asn Asp Trp Glu Asp Arg Tyr Tyr
135                 140                 145 cgt gaa aac atg tac cgc tac cct aac caa gtg tac tac agg cca gtg      595
Arg Glu Asn Met Tyr Arg Tyr Pro Asn Gln Val Tyr Tyr Arg Pro Val
150                 155                 160                 165 gat cag tac agc aac cag aac aac ttc gtg cac gac tgc gtc aat atc      643
Asp Gln Tyr Ser Asn Gln Asn Asn Phe Val His Asp Cys Val Asn Ile
```

-continued

```
                           170                 175                 180
acc atc aag cag cac acg gtc acc acc acc aag ggg gag aac ttc        691
Thr Ile Lys Gln His Thr Val Thr Thr Thr Lys Gly Glu Asn Phe
            185                 190                 195 acc gag acc gat gtg aag atg atg gag cgc gtg gtg gag cag atg tgc    739
Thr Glu Thr Asp Val Lys Met Met Glu Arg Val Val Glu Gln Met Cys
        200                 205                 210 gtc acc cag tac cag aag gag tcc cag gcc tat tac gac ggg aga aga    787
Val Thr Gln Tyr Gln Lys Glu Ser Gln Ala Tyr Tyr Asp Gly Arg Arg
    215                 220                 225 tcc agc agc acc gtg ctt ttc tcc tcc cct cct gtc atc ctc ctc atc    835
Ser Ser Ser Thr Val Leu Phe Ser Ser Pro Pro Val Ile Leu Leu Ile
230                 235                 240                 245 tcc ttc ctc atc ttc ctg atc gtg gga tga gggaggcctt cctgcttgtt      885
Ser Phe Leu Ile Phe Leu Ile Val Gly
                250 ccttcgcatt ctcgtggtct aggctggggg aggggttatc cacctgtagc tctttcaatt   945 gaggtggttc tcattcttgc ttctctgtgt cccccatagg ctaataccccc tggcactgat  1005 gggccctggg aaatgtacag tagaccagtt gctctttgct tcaggtccct ttgatggagt  1065 ctgtcatcag ccagtgctaa caccgggcca ataagaatat aacaccaaat aactgctggc  1125 tagttgggc tttgttttgg tctagtgaat aaatactggt gtatcccctg acttgtaccc   1185 agagtacaag gtgacagtga cacatgtaac ttagcatagg caaagggttc tacaaccaaa  1245 gaagccactg tttggggatg gcgccctgga aaacagcctc ccacctggga tagctagagc  1305 atccacacgt ggaattc                                                  1322
```

<210> SEQ ID NO 28
<211> LENGTH: 254
<212> TYPE: PRT
<213> ORGANISM: Mus musculus

<400> SEQUENCE: 28

```
Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Gly Ala Val Val Gly Gly Leu Gly Gly Tyr Met
        115                 120                 125

Leu Gly Ser Ala Val Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175
```

-continued

```
Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
            210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 29
<211> LENGTH: 33
<212> TYPE: PRT
<213> ORGANISM: Mus musculus

<400> SEQUENCE: 29

Met Lys His Met Ala Gly Ala Ala Ala Ala Gly Ala Val Val Gly Gly
 1               5                  10                  15

Leu Gly Gly Tyr Met Leu Gly Ser Ala Met Ser Arg Pro Met Ile His
                20                  25                  30

Phe
```